(12) United States Patent
Chun et al.

(10) Patent No.: US 11,078,130 B2
(45) Date of Patent: Aug. 3, 2021

(54) HYDROCARBON CONVERSION

(71) Applicant: ExxonMobil Chemical Patents Inc., Baytown, TX (US)

(72) Inventors: Changmin Chun, Raritan, NJ (US); Dhaval A. Bhandari, Bridgewater, NJ (US); Federico Barrai, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 37 days.

(21) Appl. No.: 16/750,764

(22) Filed: Jan. 23, 2020

(65) Prior Publication Data
US 2020/0157022 A1 May 21, 2020

Related U.S. Application Data

(62) Division of application No. 16/321,729, filed as application No. PCT/US2017/046879 on Aug. 15, 2017, now Pat. No. 10,577,292.
(Continued)

(51) Int. Cl.
*C07C 2/76* (2006.01)
*B01J 19/02* (2006.01)
(Continued)

(52) U.S. Cl.
CPC ............... *C07C 2/76* (2013.01); *B01J 6/008* (2013.01); *B01J 8/04* (2013.01); *B01J 8/0492* (2013.01);
(Continued)

(58) Field of Classification Search
CPC .... C07C 2/76; B01J 8/04; B01J 8/0496; B01J 8/067; B01J 8/0492; B01J 6/008; B01J 19/02; B01J 19/2485; B01J 2208/065; B01J 2219/2438; B01J 2208/00353; B01J 2208/00513; B01J 2219/2413; B01J 2208/00938; B01J 2219/00159; B01J 2219/2428; B01J 2219/00117; B01J 2208/0053; B01J 2208/00309;
(Continued)

(56) References Cited

U.S. PATENT DOCUMENTS 9,187,382 B2 * 11/2015 Hershkowitz ........... C07C 5/333
2008/0300438 A1 12/2008 Keusenkothen et al.
(Continued)

FOREIGN PATENT DOCUMENTS

WO 2009/009739 A 1/2009

OTHER PUBLICATIONS

Johnson et al., "Recent Developments in Ultra High Temperature Ceramics at NASA Ames", 16th AIAA/DGLR International Space Technologies Conference, Oct. 2009, pp. 1-52.
(Continued)

*Primary Examiner* — Thuan D Dang

(57) ABSTRACT

The invention relates to hydrocarbon conversion, to equipment and materials useful for hydrocarbon conversion, and to processes for carrying out hydrocarbon conversion, e.g., hydrocarbon pyrolysis processes. The hydrocarbon conversion is carried out in a reactor which includes at least one channeled member that comprises refractory and has an open frontal area≤55%. The refractory can include non-oxide ceramic.

4 Claims, 5 Drawing Sheets

Related U.S. Application Data

(60) Provisional application No. 62/381,722, filed on Aug. 31, 2016.

(51) Int. Cl.
| | | |
|---|---|---|
| *B01J 19/24* | (2006.01) | |
| *C04B 35/56* | (2006.01) | |
| *C04B 35/58* | (2006.01) | |
| *B01J 6/00* | (2006.01) | |
| *C10G 9/00* | (2006.01) | |
| *C10G 9/26* | (2006.01) | |
| *B01J 8/04* | (2006.01) | |
| *B01J 8/06* | (2006.01) | |
| *C10G 11/00* | (2006.01) | |
| *C10G 35/02* | (2006.01) | |

(52) U.S. Cl.
CPC .............. *B01J 8/0496* (2013.01); *B01J 8/067* (2013.01); *B01J 19/02* (2013.01); *B01J 19/2485* (2013.01); *C04B 35/5615* (2013.01); *C04B 35/5618* (2013.01); *C04B 35/58078* (2013.01); *C04B 35/58092* (2013.01); *C10G 9/002* (2013.01); *C10G 9/26* (2013.01); *C10G 11/00* (2013.01); *C10G 35/02* (2013.01); *B01J 2208/0053* (2013.01); *B01J 2208/00309* (2013.01); *B01J 2208/00353* (2013.01); *B01J 2208/00513* (2013.01); *B01J 2208/00938* (2013.01); *B01J 2208/065* (2013.01); *B01J 2219/00117* (2013.01); *B01J 2219/00123* (2013.01); *B01J 2219/00159* (2013.01); *B01J 2219/2413* (2013.01); *B01J 2219/2428* (2013.01); *B01J 2219/2438* (2013.01); *C04B 2235/3217* (2013.01); *C04B 2235/3225* (2013.01); *C04B 2235/3244* (2013.01); *C04B 2235/3418* (2013.01); *C04B 2235/3813* (2013.01); *C04B 2235/3826* (2013.01); *C04B 2235/3843* (2013.01); *C04B 2235/3891* (2013.01); *C10G 2400/20* (2013.01)

(58) Field of Classification Search
CPC .. B01J 2219/00123; C10G 9/002; C10G 9/26; C10G 11/00; C10G 35/02; C10G 2400/20; C04B 35/5615; C04B 35/5618; C04B 35/58078; C04B 35/58092; C04B 2235/3217; C04B 2235/3225; C04B 2235/3244; C04B 2235/3418; C04B 2235/3813; C04B 2235/3843; C04B 2235/3826; C04B 2235/3891

See application file for complete search history.

(56) References Cited

U.S. PATENT DOCUMENTS

2009/0250377 A1    10/2009    Chun et al.
2016/0176781 A1    6/2016    Hershkowitz et al.

OTHER PUBLICATIONS

Justin et al., "Ultra High Temperature Ceramics: Densification, Properties and Thermal Stability", Aerospace Lab Journal, Issue 3, Nov. 2011, pp. 1-11.

* cited by examiner

HYDROCARBON CONVERSION

CROSS REFERENCE TO RELATED APPLICATIONS

This application is a divisional of U.S. patent application Ser. No. 16/321,729, filed Jan. 29, 2019, which is a National Stage Application of International Application No. PCT/US2017/046879 filed Aug. 15, 2017, which claims the benefit of U.S. Patent Application Ser. No. 62/381,722, filed Aug. 31, 2016, which is incorporated herein by reference. Cross reference is made to the following related patent applications: U.S. Patent Application Ser. No. 62/402,009, filed Sep. 30, 2016, U.S. Patent Application Ser. No. 62/466,050, filed Mar. 2, 2017, U.S. Patent Application Ser. No. 62/486,545, filed Apr. 18, 2017, and PCT Patent Application No. PCT/US2017/046871, filed Aug. 15, 2017, which are incorporated by reference herein.

FIELD

The invention relates to hydrocarbon conversion in a flow-through reactor, to apparatus and materials useful for hydrocarbon conversion, to processes for carrying out hydrocarbon conversion reactions, e.g., hydrocarbon pyrolysis reactions. The flow-through reactor includes at least one channeled member comprising refractory and having an open frontal area≤55%. The refractory can include non-oxide ceramic.

BACKGROUND

Olefin demand continues to grow, particularly demand for light olefin such as ethylene, propylene, and butenes. Commercial light olefin production can be carried out by steam cracking a hydrocarbon-containing feed. A steam cracker includes furnace tubes located proximate to one or more burners which heat the tube's outer surface. A mixture of the feed and steam is introduced into the heated furnace tubes, and heat transferred from the furnace tube to the mixture converts at least a portion of the feed to light olefin by pyrolysis. Furnace tube heating is typically controlled in a temperature in the range of 750° C. to 900° C. to achieve a fixed, predetermined feed conversion, typically in the range of about 60% to about 80%. Although ethylene is the primary light olefin product, steam cracking also produces appreciable yields of propylene and butenes, particularly when the steam cracker's feed comprises $C_{5+}$ hydrocarbon. Since steam cracking process conditions are selected to provide a fixed, predetermined feed conversion, ethylene, propylene and butylene yields are substantially constant. Steam crackers also include facilities for recovering light olefin from the steam cracker's effluent, which besides light olefin typically further comprises one or more of molecular hydrogen, methane, ethane, propane, butanes, acetylene, butadiene, and $C_{5+}$ saturated and unsaturated hydrocarbon, including coke precursors and coke.

Introducing steam into the steam cracker feed decreases the hydrocarbon partial pressure, which lessens the amount of coke produced during the pyrolysis. The steam also reacts with coke and coke precursors during the pyrolysis, which further decreases the amount coke produced during the pyrolysis. Even with added steam, however, the pyrolysis produces an appreciable yield of coke and coke precursors, and a portion of the coke accumulates in the furnace tubes.

Accumulating coke leads to both an undesirable pressure-drop increase across the tubes' internal flow path and a decrease in heat transfer to the feed-steam mixture. To overcome these difficulties, at least a portion of accumulated coke is removed from the interior of a tube by switching the tube from pyrolysis mode to decoking mode. During decoking mode, the flow of feed-steam mixture into the coked tube is terminated, and a flow of decoking fluid is established instead. The decoking fluid, typically comprising air and/or steam, reacts with and removes the accumulated coke. When sufficient coke has been removed, the tube is switched from decoking mode to pyrolysis mode to resume light olefin production. Although periodic decoking mode operation decreases the amount of accumulated coke, this benefit is obtained at a substantial energy cost. In part to lessen damage to the furnace tubes, e.g., by repeated thermal expansion/contractions, the burners operate not only during pyrolysis mode, but also during decoking mode, even though an appreciable amount of recoverable light olefin is not produced during decoking mode.

In order to increase energy efficiency and improve the yield of light unsaturated hydrocarbon, processes have been developed which carry out pyrolysis and other reactions in a regenerative reactor. Such reactors generally include a regenerative member having at least one internal channel (a channeled member). The channeled member is preheated, and then a flow of the hydrocarbon-containing feed is established through the channel. Heat is transferred from the channeled member to the hydrocarbon feed, which increases the hydrocarbon feed's temperature and converts the feed via the desired reaction and side reactions. When the reaction is pyrolysis, the pyrolysis product typically comprises molecular hydrogen, methane, acetylene, ethylene, and $C_{3+}$ hydrocarbon, the $C_{3+}$ hydrocarbon being primarily in the form of coke and coke precursors. At least a portion of the coke remains in the passages of the channeled member, and the remainder of the pyrolysis product is conducted away from the reactor as a pyrolysis effluent. Ethylene is typically recovered from the pyrolysis effluent downstream of the reactor. Since pyrolysis is on-average endothermic, pyrolysis mode operation will eventually cool the channeled member, e.g., to a temperature below which the pyrolysis reactions substantially terminate. The ability to carry out pyrolysis reactions is restored by regenerating the channeled member during a heating mode. During heating mode, the flow of hydrocarbon-containing feed to the regenerative pyrolysis reactor is terminated. Flows of oxidant and fuel are established to the reactor, typically in a direction that is the reverse of the feed flow direction, and heat is transferred from combustion of the fuel and oxidant to the channeled member for reheating. After the reactor is sufficiently reheated, the reactor is switched from heating mode to pyrolysis mode.

U.S. Patent Application Publication No. 2016-176781 discloses increasing ethylene yield from a regenerative pyrolysis reactor by operating pyrolysis mode in an elongated tubular regenerative pyrolysis reactor. The reference (e.g., in its FIG. 1A) discloses controlling the pyrolysis mode for increased ethylene selectivity and decreased selectivity for coke and methane by establishing a sharp thermal gradient in the bulk gas temperature profile between a region of substantially constant temperature at which the pyrolysis can occur and a substantially constant lower temperature at which pyrolysis does not occur. During pyrolysis, the position of the gradient within the tubular reactor moves inward as the reactor cools, i.e., toward the midpoint of the reactor's long axis. The cooled reactor is then switched to heating mode, during which the gradient moves outward, i.e., away from the midpoint of the reactor's long axis. Although utilizing such pyrolysis conditions results in a coke yield that is less than that of steam cracking, some coke does accumulate in the channel. Advantageously, the reference reports that accumulated coke can be oxidized to volatile products such as carbon dioxide during heating mode by combusting oxidant in the oxidant flow. Energy efficiency is increased over steam cracking because (i) heating is not needed during pyrolysis mode and (ii) heat released by coke combustion in passages of the channeled member during heating mode aids channeled member regeneration. Although the process is more energy efficient than steam cracking, maintaining a sharp temperature gradient in the bulk gas temperature profile leads to substantially constant ethylene and $C_{3+}$ hydrocarbon selectivities along the length of the pyrolysis zone. Moreover, since the sharp gradient moves downstream during the pyrolysis, the substantially constant ethylene and $C_{3+}$ selectivities are maintained along the length of the pyrolysis zone for the duration of pyrolysis mode.

Energy efficient processes are now desired which have flexibility to produce a range of product selectivities in the reaction zone during a reaction mode, e.g., a range of light olefin selectivities in the pyrolysis zone during pyrolysis mode, particularly processes which exhibit appreciable feed conversion without excessive coke yield.

SUMMARY OF THE INVENTION

The invention is based in part on the discovery that regenerative reactors can be operated to produce a range of product selectivities in a reaction zone during a reaction mode such as pyrolysis mode, with appreciable feed conversion and without excessive byproduct yield, such as excessive coke yield. Contrary to the teachings of the prior art, it has been found to be beneficial to establish a bulk gas temperature profile during the pyrolysis that does not exhibit a sharp gradient between a substantially constant higher temperature region and a substantially constant lower temperature region.

It also has been found to be beneficial for certain features of the bulk gas temperature profile to exhibit a temperature decrease of ≤100° C. during the course of reactions such as pyrolysis. Doing so provides yields of desirable products which do not vary appreciably as a function of time during the reaction, leading to a significant simplification of product recovery and purification systems located downstream of the reactor. For a wide range of reactions and process conditions and commercially-significant feed rates, these desirable characteristics of the bulk gas temperature profile can be achieved when the reactor includes a channeled member having an open frontal area≤55%.

The invention is also based in part on the discovery that a channeled member having an open frontal area≤55% and comprising certain refractories which include non-oxide ceramics can survive long-term under process conditions encountered in a wide range of reactions. e.g., hydrocarbon pyrolysis. It has been found that the channeled member and other reactor components comprising the specified ceramics have (i) sufficient resistance to thermal shock, and (ii) sufficient chemical and structural stability, e.g., resistance to oxidation and carburization, so as to survive repeated temperature swings and changing chemical environments in reaction mode and heating mode during prolonged operation.

Accordingly, certain aspects of the invention relate to reacting a feed comprising hydrocarbon in at least one flow-through reactor. The reactor has opposed first and second openings and an internal volume. The internal volume includes a channeled member having an open frontal area≥55%. The channeled member has opposed first and second apertures and at least one internal channel. The second aperture is separated from the first aperture by a flow-path through the channel. The channeled member is positioned in the reactor so that the first opening is adjacent to the first aperture. The channeled member comprises at least one refractory which includes one or more of (i) a first ceramic comprising at least one compound represented by the formula $M_{n+1}AX_n$, (ii) a second ceramic comprising at least one compound represented by the formula $N_iB_j$, and (iii) a third ceramic comprising at least one compound represented by the formula $P_kQ_m$. In these formulas, M is at least one element selected from Groups 3-6 of the Periodic Table; A is at least one element selected from Groups 13-16 of the Periodic Table; X is carbon and/or nitrogen; N is at least one element selected from Groups 4 and 5 of the Periodic Table; B is boron, P is at least one element selected from Groups 4-10 of the Periodic Table, Q is silicon and/or aluminum; n is 1, 2, or 3; i and k are each a positive integer; j is i+1 or i+2; and m is a positive integer that can be greater than k, less than k, or equal to k.

The process includes also includes operating the reactor in heating mode during a heating time $t_H$. During heating mode, the channeled member is heated to achieve an average temperature $T_{av}$ in the range of from 500° C. to 1400° C. The process continues by carrying out a feed conversion reaction during reaction mode operation for a reaction time $t_R$. During reaction mode, a flow of the feed is established from the first opening, through the first aperture, and into the internal channel. The feed reacts in the channel to produce a reaction product which is conducted out of the channel, through the second aperture, and away from the reactor via the second opening. $T_{av}$ decreases by no more than 100° C. during $t_R$.

In other aspects, the invention relates reactors and reactor components used in such processes, and to reaction products produced by such processes.

DETAILED DESCRIPTION

Figure 1:
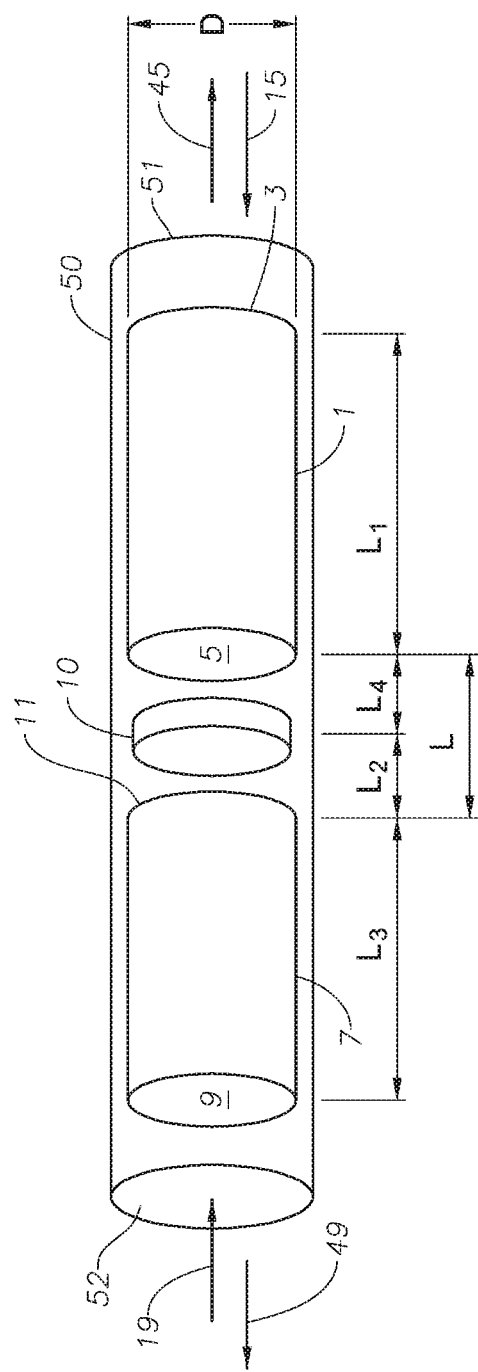
FIG. 1 schematically shows one form of a reverse flow reactor that is suitable for carrying out certain aspects of the invention.

The invention relates to carrying out reactions such as endothermic hydrocarbon conversion reactions in flow-through reactors such as regenerative, reverse-flow reactors. Reactions encompassed by the invention include one or more of steam reforming, dry ($CO_2$) reforming, pyrolysis, catalytic cracking, dehydrogenation, isomerization, disproportionation, alkylation, de-alkylation, and dehydration. Examples of selected reactions and suitable process conditions for carrying them out are described in U.S. Patent Application Publication No. 2008-0142409, which is incorporated by reference herein in its entirety.

In the following portion of this description, the invention will be described with reference to aspects where the reaction includes hydrocarbon pyrolysis carried out in a regenerative pyrolysis reactor. In these aspects, the reaction mode is pyrolysis mode, and the reaction time $t_R$ is the pyrolysis time $t_P$. The invention is not limited to these aspects, and this description is not meant to foreclose other aspects within the broader scope of the invention. This description and appended claims include certain terms which are defined as follows.

Definitions

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing≤1% (molar basis) of unsaturated carbon atoms. The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the pair's carbon atoms are directly linked by a double bond. The term "aromatics" and "aromatic hydrocarbon" mean hydrocarbon compounds containing at least one aromatic ring.

The terms "reactor", "reactor system", "regenerator", "recuperator", "regenerative bed". "monolith", "honeycomb", "reactant", "fuel", and "oxidant" have the meanings disclosed in U.S. Pat. No. 7,943,808, which is incorporated by reference herein in its entirety. A "pyrolysis reactor" is a reactor, or combination of reactors or a system for hydrocarbon pyrolysis. The term "pyrolysis stage" means at least one pyrolysis reactor, and optionally including means for conducting one or more feeds thereto and/or one or more products away therefrom. A "region" or "zone" is a location, e.g., a specific volume, within a reactor, a location between two reactors and/or the combination of different disjointed locations in one or more reactors. A "pyrolysis region" is a location where pyrolysis is carried out, e.g., in a location which contains or is proximate to components, such as at least one thermal mass, which provides heat for the pyrolysis. A reactor or reaction stage can encompass one or more reaction regions. More than one reaction can be carried out in a reactor, stage, or region.

A pyrolysis region can include components, e.g., one or more members of appreciable heat capacity having conduits, channels, and passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a channeled member can have the form of a honeycomb monolith comprising a single channel, with the channel having a plurality of passages or sets of passages.

The pyrolysis reactor includes at least one channeled member (e.g., a flow-control component) comprising refractory. The channeled member can function as a thermal mass, e.g., for storing heat during heating mode and releasing heat during reaction mode. The refractory has a mass density $\rho_s$, referred to herein as a "solid density", and a heat capacity $C_p$ (measured at 25° C.) that is typically ≥0.05 cal./g ° C. The channeled thermal mass has an open frontal area ("OFA") for passing fluid into the channel(s), where OFA has the same meaning as in U.S. Pat. No. 5,494,881, which is incorporated by reference herein in its entirety.

The term "bulk gas temperature" means the temperature of a bulk gas steam as measured by a device (such as a thermocouple) that is in contact with the bulk gas but not in contact with a solid such as the channeled member's refractory. For example, if the gas is traveling through an internal channel of length $L_c$ of a channeled member in the pyrolysis zone of a thermal pyrolysis reactor, the bulk gas temperature at a location along $L_c$ is the average temperature (arithmetic mean) over the channel's cross sectional area at that location. The peak gas temperature ("$T_p$") is the greatest cross-sectional-averaged bulk gas temperature achieved along a flowpath, e.g., within a passage of a channel. When the thermal profile over the length of a flow path exhibits more than one local maximum, $T_P$ corresponds to the local maximum having the greatest bulk gas temperature. One skilled in the art will appreciate that a gas temperature immediately proximate to a solid thermal mass, such as a partition between passages within a thermal mass at any particular location may exceed the bulk gas temperature, and may, in some infinitesimal layer, actually approach the solid's temperature. The average bulk gas temperature "$T_{av}$" over a region of the reactor. e.g., of the pyrolysis zone, is obtained using the formula:

$$Tav = \left[\frac{1}{b-a}\int_a^b T(x)dx\right]$$

Figure 2:
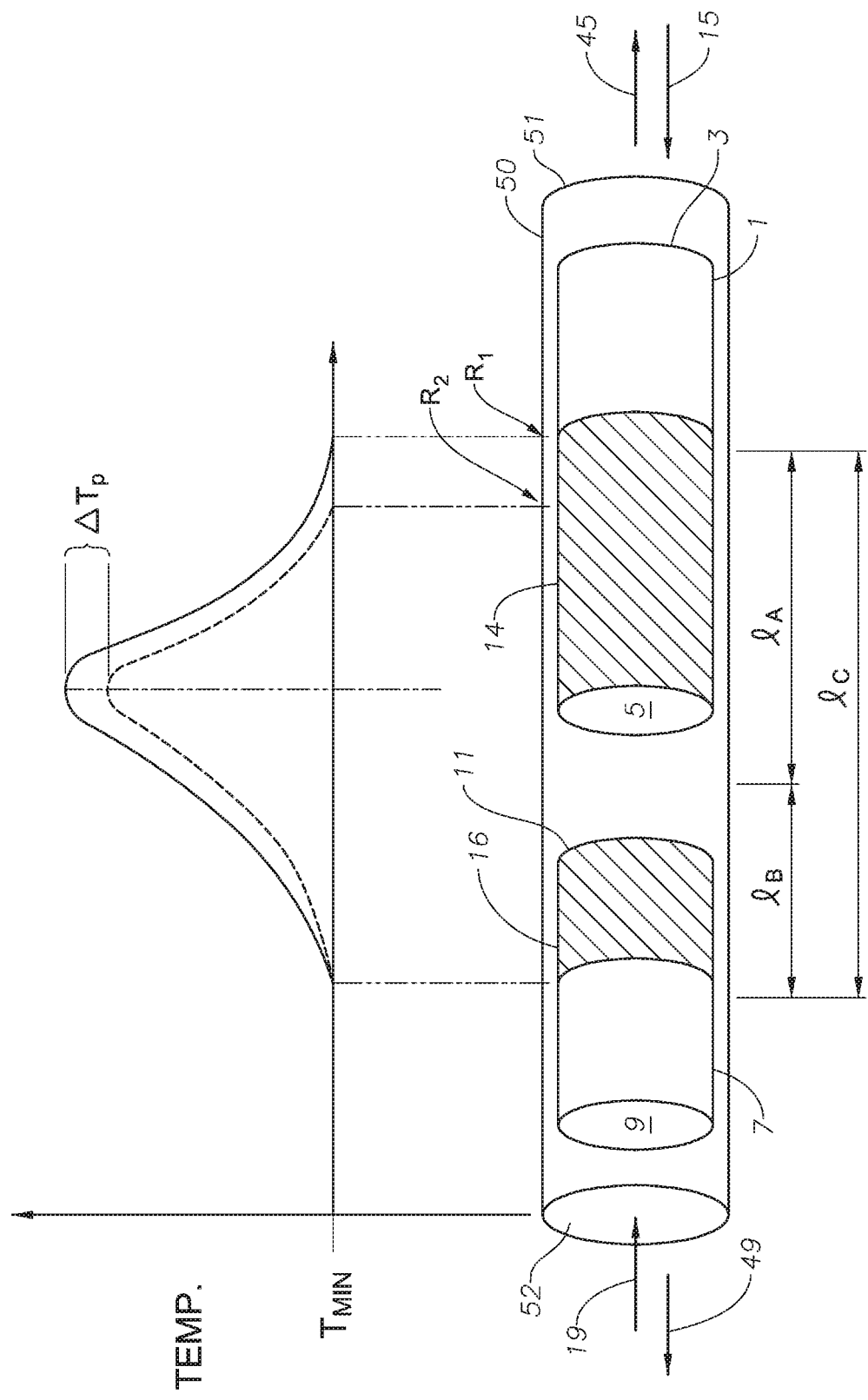
FIGS. 2 and 3 schematically show forms of a reverse flow reactor and representative bulk gas temperature profiles at the start (solid lines) and end (dashed lines) of pyrolysis mode.
Figure 3:
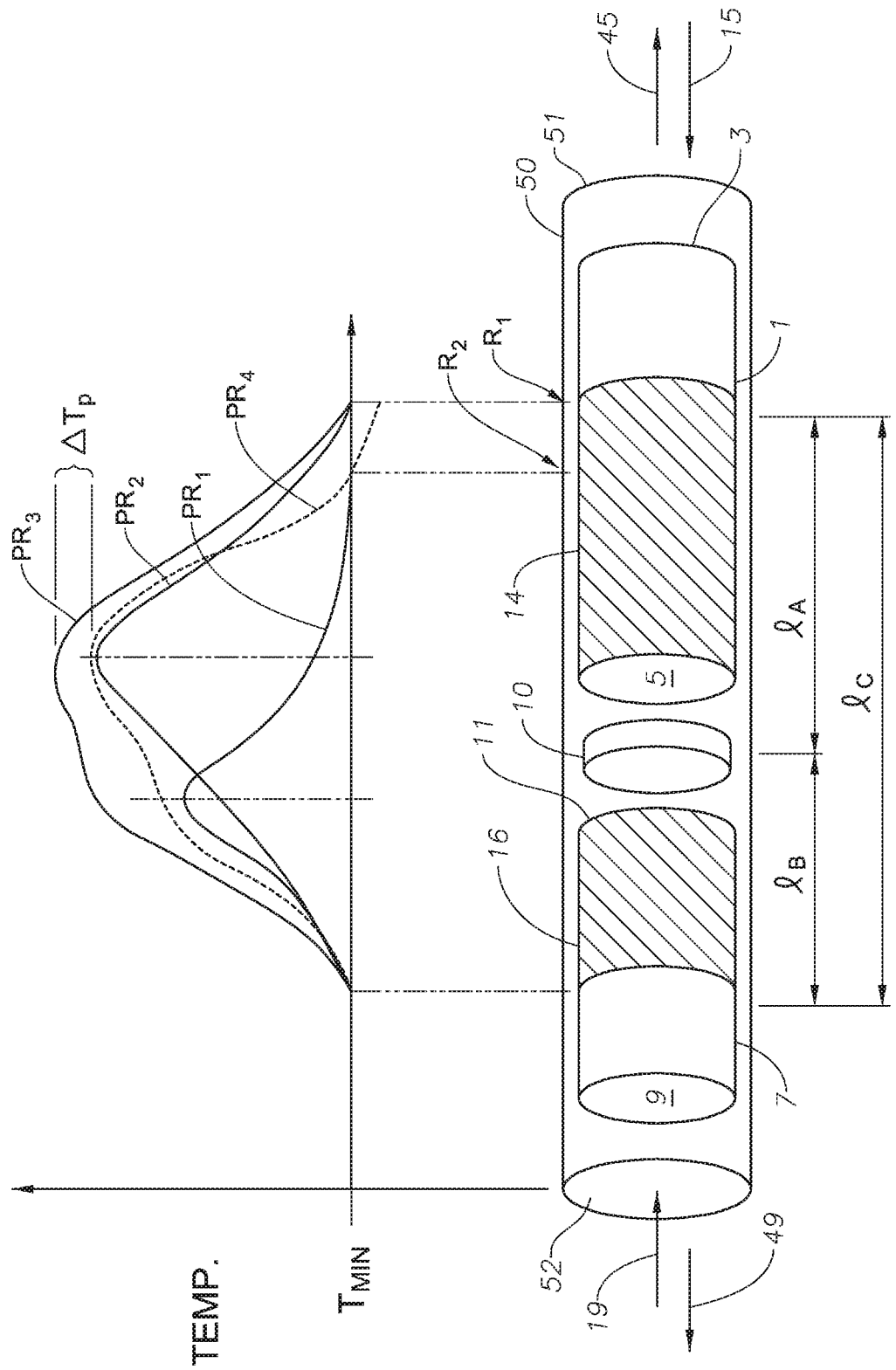

Parameters a and b are the boundaries of an interval (distance) along the long axis of the reactor. For example, referring to FIG. 1, parameter "a" can be the position of aperture 50 and parameter "b" can be the position of aperture 9. T(x) is a function representing the variation of bulk gas temperature over the interval of from a to b. When T(x) is a bulk gas temperature profile of a pyrolysis zone, e.g., the pyrolysis zones indicated (at the start of $t_P$) by the shaded regions in FIGS. 2 and 3, parameters a and b are the locations where the bulk gas temperature profile intersects the line $T_{MIN}$, which corresponds to the minimum temperature at which feed conversion is ≥10% under the selected pyrolysis conditions and feed. Since the bulk gas temperature profile typically changes during the pyrolysis time interval $t_P$, as shown in FIGS. 2 and 3, $T_{av}$ will typically decrease during $t_P$. The portion of the profile having a temperature$\geq T_{MIN}$, can be continuous, but this is not required. For example, when a profile that intersects $T_{MIN}$ at more than two locations in the pyrolysis zone (e.g., a, b) and touches $T_{MIN}$ at a location c (not shown, but between a and b), additional integrations are carried out, e.g.:

$$Tav = \frac{1}{b-1}\int_a^b T(x)dx + \frac{1}{c-b}\int_b^c T(x)dx.$$

When the portion of the profile that is $\geq T_{MIN}$ is in the form of discrete segments, the integrations are performed over each of the segments. Those skilled in the art will appreciate that bulk gas temperature profile can be approximated by a set of discrete bulk gas temperatures measured at selected locations along the length of the pyrolysis zone, e.g., about ten locations, such as 20 locations, or 50 locations. $T_{av}$ can be approximated by summing the discrete bulk gas temperature measurements in the set and dividing the sum by the number of discrete bulk gas temperature measurements in the set.

The term "selectivity" refers to the production (weight basis) of a specified compound in a reaction. As an example, the phrase "a hydrocarbon pyrolysis reaction has 100% selectivity for methane" means that 100% of the hydrocarbon (weight basis) that is converted in the pyrolysis reaction is converted to methane. When used in connection with a specified reactant, the term "conversion" means the amount of the reactant (weight basis) consumed in the reaction. For example, when the specified reactant is ethane, 100% conversion means 100% of ethane is consumed in the reaction. With respect to hydrocarbon pyrolysis the term "conversion" encompasses any molecular decomposition by at least pyrolysis heat, including cracking, breaking apart, and reforming. Average conversion in a reaction zone. e.g., a pyrolysis zone, is the conversion achieved at TN. Yield (weight basis) is conversion times selectivity.

The term "pyrolysis" means an endothermic reaction for converting molecules into (i) atoms and/or (ii) molecules of lesser molecular weight, and optionally (iii) molecules of greater molecular weight, e.g., processes for converting ethane and/or propane to molecular hydrogen and unsaturates such as ethylene, propylene and acetylene. Certain aspects of the invention feature a pyrolysis zone exhibiting selectivities (e.g., of desired products) which vary as a function of position along the length of the pyrolysis zone but which do not vary appreciably as a function of time during pyrolysis mode, e.g., within about +/−25%, such as +/−10%, or +/−5% from selectivity at the start of $t_P$. More particularly, for certain aspects in which $T_{av}$ and/or $T_p$ decrease by $\leq 100°$ C. during pyrolysis mode, the yield of many desired products, e.g., light olefin yield, such as ethylene and/or propylene yield, do not vary appreciably as a function of time during pyrolysis mode even though the product selectivities vary as a function of position along the length of the pyrolysis zone. For example, yield is typically within about +/−25%, such as +/−10%, or +/−5% of yield at the start of $t_P$. In these aspects, average conversion might not vary appreciably as a function of time during pyrolysis mode, and is typically within about +/−25%, such as +/−10%, or +/−5% of average conversion at the start of $t_P$.

A hydrocarbon feed is subjected to "thermal pyrolysis" when <50.0% of the heat utilized by the pyrolysis is provided by exothermically reacting the hydrocarbon feed, e.g., with an oxidant. The invention encompasses forms of thermal pyrolysis wherein $\leq 40.0\%$ of the heat utilized by the pyrolysis is provided by exothermically reacting the hydrocarbon feed, e.g., $\leq 25.0\%$, such as $\leq 10.0\%$. In certain aspects, substantially no heat for the pyrolysis is provided by exothermically reacting the hydrocarbon feed. The "severity threshold temperature" for pyrolysis is the lowest bulk gas temperature at which acetylene selectivity is at least 10% for a total residence time$\leq 0.1$ second. High-severity pyrolysis conditions are those carried out at a peak gas temperature that is greater than or equal to the severity threshold temperature. Low-severity pyrolysis conditions are those carried out at a peak gas temperature that is less than the severity threshold temperature, i.e. conditions under which substantially no hydrocarbon pyrolysis is carried out at a pyrolysis gas temperature that exceeds the severity threshold temperature. High-severity conditions include those which exhibit (i) a methane selectivity$\geq 5$ wt. % and/or (ii) a propylene selectivity at a temperature$\geq 1000°$ C. of $\leq 0.6$ wt. %. With respect to pyrolysis reactors, the term "total residence time" means the average time duration for substantially non-reacting (non-converting by pyrolysis) molecules (such as He, $N_2$, Ar) having a molecular weight in the range of 4 to 40 to traverse a pyrolysis region of a pyrolysis reactor. The term "gas residence time" means the residence time average time of a substantially non-liquid molecules.

The term "Periodic Table" means the Periodic Chart of the Elements, as it appears on the inside cover of The Merck Index, Twelfth Edition, Merck & Co., Inc., 1996.

Certain aspects of the invention relate to carrying out pyrolysis mode and heating mode under the specified conditions in one or more reverse flow reactors. Representative reverse flow reactors will now be described in more detail with respect to FIG. 1. The invention is not limited to these aspects, and this description is not meant to foreclose the use of other reactors within the broader scope of the invention.
Representative Reverse Flow Reactors Reverse-flow reactor 50 can be in the form of an elongated tubular vessel having an internal volume which includes a pyrolysis zone for carrying out the pyrolysis. Typically, the internal volume includes three zones: a first heat-transfer zone, a second heat transfer zone, with the pyrolysis zone being located between the first and second heat transfer zones. The zones are in fluidic communication with one another. The reactor vessel's cross sectional shape and/or cross sectional area can be substantially uniform over the length of the reactor, but this is not required. For example, one or more segments of the reactor vessel's length can have a circular, elliptical, or polygonal cross section. Reactor 50 has opposed first and second openings 51 and 52 which are in fluidic communication with the internal volume and are located at terminal ends of the reactor vessel.

The reactor 50 includes first and second channeled members 1 and 7 for transferring heat to/from reactants and products during the pyrolysis and heating modes. The geometric form (size, shape, cross-sectional area) of the channeled members can be similar to those disclosed as regenerative beds in U.S. Pat. Nos. 8,754,276; 9,126,882; 9,346.728; 9,187,382; 7,943,808; 7,846.401; 7,815,873; 9,322,549; and in U.S. Patent Application Publications Nos. 2007-0144940, 2008-300438, 2014-303339, 2014-163287, 2014-163273, 2014-0303416, 2015-166430, 2015-197696, and 2016-176781. These references are incorporated by reference herein in their entireties.

It has been found that in order to keep $T_p$ and/or $T_{av}$ from decreasing by no more than about 100° C., and preferably $\leq 75°$ C. during $t_P$ under a wide range of pyrolysis conditions, the OFA of at least channeled member 1 should be $\leq 55\%$, e.g., ≤45%, such as ≤40%, or ≤35%. Although channeled members having a very small OFA are within the scope of the invention, it has been found that an OFA of less than about 25%, and particularly less than about 10%, can result in an undesirably large pressure drop across the reactor. Typically, the OFA of channeled member 1 is (i) ≥10%, e.g., ≥15%, such as ≥20%, or ≥25%, or ≥30%; and (ii) ≤55%, e.g., ≤50%, such as ≤45%, or ≤40%, or ≤35%. For example, OFA can be in the range of about 10% to 55%, e.g., 15% to 50%, such as 20% to 45%, or 25% to 35%. The first channeled member comprises at least one refractory. Typically, the first channeled member comprises ≥75 wt. % of the refractory, based on the weight of the first channeled member, e.g., ≥95 wt. %, such as ≥99 wt. %. Typically, the refractory comprises ≥50 wt. % of non-oxide ceramic, e.g., refractory which before the start of a first heating mode comprises <50 wt. % of ceramic in the form of one or more oxide of one or more metal. More typically, the refractory comprises ≥75 wt. % of non-oxide ceramic, e.g., ≥90 wt. %, such as ≥95 wt. %. In certain aspects, the refractory is substantially free of ceramic in the form of one or more oxide of one or more metals, e.g., comprises ≤1 wt. % of oxide of one or more metals, such as ≤0.1 wt. %, or ≤0.01 wt. %.

In certain aspects, the first channeled member comprises a refractory which includes one or more of a first ceramic, a second ceramic, and a third ceramic. The first ceramic comprises at least one compound represented by the formula $M_{n+1}AX_n$, the second ceramic comprises at least one compound represented by the formula $N_iB_j$, and the third ceramic comprises at least one compound represented by the formula $P_kQ_m$. In these formulas, M is at least one element selected from Groups 3-6 of the Periodic Table; A is at least one element selected from Groups 13-16 of the Periodic Table; X is carbon and/or nitrogen; N is at least one element selected from Groups 4 and 5 of the Periodic Table; B is boron, P is at least one element selected from Groups 4-10 of the Periodic Table, Q is silicon and/or aluminum; n is 1, 2, or 3; i and k are each a positive integer; j is i+1 or i+2; and m is a positive integer that can be greater than k, less than k, or equal to k. Generally, M is selected from the group consisting of Sc, Ti, Zr, Hf, V, Nb. Ta, Cr, Mo, and combinations thereof; A is selected from the group consisting of Al, Si, P, Ga, Ge, As, Cd, In, Sn, Tl, Pb, and combinations thereof; N is selected from the group consisting of Ti, Zr, Hf, V, Nb, Ta, and combinations thereof; P is selected from the group consisting of Ti, Zr, Hf, V. Nb, Ta, Cr, Mo, W, Mn, Tc, Re, Fe, Ru, Os, Co, Rh, Ir, Ni, Pd, Pt, and combinations thereof; and m is ≤k. Typically, the first ceramic comprises one or more of $Ti_3SiC_2$, $Ti_2AlC$, $Nb_2AlC$, $Zr_2AlC$, $Ti_2AlC$, $V_2AlC$, $Cr_2AlC$, $Hf_2InC$, $Ti_2SC$, $V_2SC$, $Ti_3SiC_2$, $Ti_3GeC_2$, $Ti_3SnC_2$, $Ti_3AlC_2$, $Ti_2AlC$, $Ti_2AlN$, $Ti_3AlC$, $Ti_3AlN_2$, $(Nb,Zr)_2AlC$, $(Ti,V)_2AlC$, $(Ti,Nb)_2AlC$, $(Ti,Cr)_2AlC$, $(Ti,Hf)_2InC$, and $(Ti,V)_2SC$, $Ti_3(Si,Ge)C_2$, and $Ti_3(Sn,Al)C_2$, $Ti_2Al(C,N)$ and $Ti_3Al(C,N)_2$. Typically, the second ceramic comprises $ZrB_2$ and/or $HfB_2$; and the third ceramic comprises $Nb_3Al$, $Nb_2Al$, $NbAl$, $NbAl_3$, and $MoSi_2$.

The first ceramic, commonly referred to as "MAX" ceramic, includes members of a class of ternary carbides and nitrides having a layered hexagonal structure. If desired, the first ceramic can further comprise one or more secondary phases. Such secondary phases, when present, include one or more of intermetallics, oxides, carbides, nitrides, oxycarbides, oxynitrides, and carbonitrides of at least one metal selected from the group consisting of Ti, Zr, Hf, V, Nb, Ta, Cr, Mo. W, Mn, Tc, Re, Fe, Ru, Os, Co, Rh, Ir, Ni, Pd, Pt, Al, Si, Y, and La. When used, the amount of such secondary phases is in the range of from 0.1 to 20 vol. %, based on the weight of the first ceramic, e.g., in the range of 0.1 to 10 vol. %. In certain aspects, secondary phases are not used. For example, the first ceramic can contains <0.1 vol. % of secondary phases, e.g., <0.01 vol. %. Suitable first ceramics include $Ti_3SiC_2$ and $Ti_2AlC$, which are believed to be particularly resistant to oxidation during heating mode as a result of formation of a protective oxide layer ($Al_2O_3$ in the case of $Ti_2AlC$). Suitable methods for producing the first ceramics can be found in *Layered Machinable and Electrically Conductive Ti2AlC, and Ti3AlC2 Ceramics: a Review*, X. H. Wang et al.: J. Mater. Sci. Technol., 2010, 26(5), 385-416, which is incorporated by reference herein in its entirety.

The second ceramic includes members of a group commonly referred to as Ultra-High Temperature Ceramic ("UHTC"), which typically have a melting point in the range of from 2500° C. to 3000° C. If desired, the second ceramic can further comprise one or more secondary phases, e.g., to improve oxidation resistance and facilitate easy fabrication. Such secondary phases, when present, include one or more of intermetallics, oxides, carbides, nitrides, oxycarbides, oxynitrides, and carbonitrides of at least one metal selected from the group consisting of Ti, Zr, Hf, V, Nb, Ta, Cr, Mo, W, Mn, Tc, Re, Fe, Ru, Os, Co, Rh, Ir, Ni, Pd, Pt, Al, Si, Y, La. When used, the amount of such secondary phases is typically in the range of from 5 to 50 vol. %, e.g., 20 to 40 vol. %. In certain aspects, secondary phases are not used. For example, the second ceramic can contains <0.1 vol. % of secondary phases, e.g., <0.01 vol. %. As an example, one suitable second ceramic comprises 20 vol. % SiC and 20 vol. % $TaSi_2$, based on the volume of the second ceramic, where ≥50 vol. % of the remainder of the second ceramic comprises $ZrB_2$, e.g., ≥75 vol. %, such as ≥90 vol. %, or ≥95 vol. %. Suitable methods for producing the second ceramics can be found in *Refractory Diborides of Zirconium and Hafnium*, J. Am. Ceram. Soc., 90 [5] 1347-1364 (2007), which is incorporated by reference herein in its entirety.

The third ceramic includes members of a group of intermetallic materials (e.g., intermetallic alloys and intermetallic compounds) commonly referred to as "intermetallics". If desired, the third ceramic can further comprise one or more secondary phases to improve toughness and to facilitate easy fabrication, e.g., secondary phases represented by the formula $P'_aQ_b$. P' is at least one element selected from the groups between IV and VIII of the periodic table, Q is silicon and/or aluminum, a is a positive integer, and b is a positive integer that can be greater than a, less than a, or equal to a. Typically, P' is one or more of Ti, Zr, Hf, V, Nb, Ta, Cr, Mo, W, Mn, Tc, Re, Fe, Ru, Os, Co, Rh, Ir, Ni, Pd, and Pt. Optionally, the secondary intermetallic materials are derived from the intermetallic materials $P_kQ_m$ during manufacturing of the third ceramic. For example, when $NbAl_3$ is fabricated by a melting and solidification process, $Nb_2Al$ can be precipitated as a secondary intermetallic phase. When used, the amount of such secondary phases is in the range of from 0.1 to 20 vol. %, based on the weight of the first ceramic, e.g., in the range of 0.1 to 10 vol. %. In certain aspects, secondary phases are not used. For example, the first ceramic can contains <0.1 vol. % of secondary phases, e.g., <0.01 vol. %. In addition to or as an alternative to the secondary phase, the third ceramic can further comprise one or more tertiary phases, e.g., for improved toughness and to facilitate ceramic and refractory processing. When used, the tertiary phases have the form of one or more oxides, carbides, nitrides, oxycarbides, oxynitrides, and carbonitrides of at least one metal selected from the group consisting of Ti, Zr, Hf, V, Nb, Ta, Cr, Mo, W, Mn, Tc, Re, Fe, Ru, Os, Co, Rh, Ir, Ni, Pd, Pt, Al, Si, Y, and La. When used, the amount of such tertiary phases is in the range of from 0.1 to 20 vol. %, based on the weight of the third ceramic, e.g., in the range of 0.1 to 10 vol. %. In certain aspects, tertiary phases are not used. For example, the third ceramic can contain <0.1 vol. % of tertiary phases, e.g., <0.01 vol. %. As an example, one suitable third ceramic is a composite comprising $MoSi_2$ and at least one of the specified tertiary phases. A particular third ceramic comprises 90 vol. % $MoSi_2$, wherein ≥50% of the balance of the third ceramic's volume is $Al_2O_3$, e.g., ≥75%, such as ≥90%. Suitable methods for producing the third ceramics can be found in *A Comparative Overview of Molybdenum Disilicide Composites*, A. K. Vasudevan, et al., Materials Science and Engineering, A155 (1992) 1-17, which is incorporated by reference herein in its entirety.

Typically, the refractory comprises ≥75 wt. % of one or more of the first, second, and third ceramic, based on the weight of the refractory, e.g., ≥95 wt. %, such as ≥99 wt. %. Such a refractory generally has a specific heat capacity at 300° K that is ≥0.04 [kj/(° K kg)] and a mass density≥3000 kg/m$^3$. For example, the refractory's specific heat capacity at 300° K can be in the range of from 0.04 [kj/(° K kg)] to 1.2 [kj/(° K kg)]. The refractory's mass density can be in the range of from 3 g/cm$^3$ to 7 g/cm$^3$, typically 5 g/cm$^3$ to 7 g/cm$^3$, and more typically in the range of from 6 g/cm$^3$ to 7 g/cm$^3$. Typically, the refractory has thermal conductivity in the range of from 0.5 W/m° K to 50 W/m° K, and a coefficient of thermal expansion in the range of from $1 \times 10^{-7}/°$ K to $2 \times 10^{-5}$/K. The refractory can have a melting point at atmospheric pressure that is ≤2000° C., e.g., in the range of from 2500° C. to 3000° C.

It has been found that a first channeled member comprising the specified refractory has desirable properties which make it particularly suitable for use in regenerative pyrolysis reactors, particularly in regenerative-reverse-flow pyrolysis reactors. Such a channeled member can withstand repeated thermal cycling over alternating heating and pyrolysis modes, e.g., a $\Delta T_{av}$ of 100° C. at a $T_p \geq 800°$ C. or ≥1100° C., or even ≥1,350° C. for 10,000 cycles with no substantial spallation or cracking. The first channeled member typically has an average wetted surface area per unit volume in the range of from 1 cm$^{-1}$ to 100 cm$^{-1}$. The internal channel of the first channeled member typically includes a plurality of substantially parallel passages, e.g., at a passage density in the range of from 77000/m$^2$ to $1.3 \times 10^6$/m$^2$.

Although the second channeled member can be of substantially the same composition as the first channeled member, this is not required. In certain aspects, the second channeled member comprises bedding or packing material that is effective in storing and transferring heat, such as glass or ceramic beads or spheres, metal beads or spheres, ceramic (e.g., ceramics, which may include, e.g., alumina, yttria, and zirconia) or honeycomb materials comprising ceramic and/or metal, other forms of tubes comprising ceramic and/or metal, extruded monoliths and the like. The choice of refractory for the second channeled member is not critical, provided it is capable of surviving under pyrolysis mode and heating mode conditions for practical run lengths (e.g., months) without significant deterioration or decomposition. The compositions of the second channeled member is typically selected to substantially maintain integrity (structural and compositional) and functionality during long term exposure to pyrolysis feeds, products, and reaction conditions, e.g., temperatures≥750° C., such as ≥1200° C., or for increased operating margin≥1500° C. Conventional refractories can be used, including those comprising at least one oxide of one or more elements selected from Groups 2-14 of the Periodic Table, but the invention is not limited thereto. In particular aspects, the refractory includes oxide of at least one of Al, Si, Mg, Ca, Fe, Mn, Ni, Co, Cr, Ti, Hf, V, Nb, Ta, Mo, W, Sc, La, Yt, Zr, and Ce.

Optionally, the second channeled member has substantially the same size, shape, cross-sectional area, thermal properties, OFA, and passage density as the first channeled member, but this is not required. For example, the second channeled member can have a thermal conductivity in the range of from 0.5 W/m° K to 50 W/m° K, a coefficient of thermal expansion in the range of from $1 \times 10^{-7}/°$ K to $2 \times 10^{-5}/°$ K. and an average wetted surface area per unit volume in the range of from 1 cm$^{-1}$ to 100 cm$^{-1}$. The internal channel of the second channeled member typically includes a plurality of substantially parallel passages, e.g., at a passage density in the range of from 77000/m$^2$ to $1.3 \times 10^6$/m$^2$. The channeled member comprises refractory, the refractory generally having a specific heat capacity at 300° K that is ≥0.04 [kj/(° K kg)] and a mass density≥3 g/cm$^3$. For example, the refractory's specific heat capacity at 300° K can be in the range of from 0.04 [kj/(° K kg)] to 1.2 [kj/(° K kg)], and its mass density can be in the range of from 3 g/cm$^3$ to 5 g/cm$^3$.

Generally, a first segment of the first channeled member 1 is located in the first heat transfer zone, with a second segment being located in the pyrolysis zone. Likewise, a first segment of the second channeled member can be located in the second heat transfer zone, with a second segment being located in the pyrolysis zone. Typically, channeled members 1 and 7 have the form of an elongated tubular article comprising refractory and having at least one internal channel and opposed apertures in fluidic communication with the internal channel(s). Channeled member 1 has a length $L_1$, and typically $L_1$ is substantially the same as the length of the internal channel, L. Channeled member 7 has a length $L_3$, and typically $L_3$ is substantially the same as the length of the internal channel, $L_c$. $L_1$ (and also typically $L_3$) is generally ≥0.1 times the total length of reactor 50 ($L_R$). $L_R$, is typically in the range of from $0.1*L_R$ to $0.9*L_R$ such as $0.1*L_R$ to $0.4*L_R$. Optionally, $L_3$ is of substantially the same length as $L_1$, and is of substantially the same cross-sectional shape and of substantially the same cross sectional area. As shown in FIG. 1, channeled member 1 includes first and second apertures 3 and 5, and channeled member 7 includes first and second apertures 9 and 11. Aperture 3 is adjacent to opening 51. Optionally, particularly in aspects (not shown) in which channeled member 7 is omitted, aperture 5 can be adjacent to opening 52. In the aspects illustrated in FIG. 1, channeled members 1 and 7 can each have the form of an elongated honeycomb comprising at least one channel, the channel having a plurality of passages. When a channeled member is a segmented channeled member, the honeycombs can be arranged adjacent to one another (e.g., end-to-end, in series). Since it tends to lessen reactor pressure drop, it is typically desirable to a align passages of a honeycomb's internal channel or channels with those of neighboring honeycombs to facilitate fluidic communication through the channeled member. Optionally, the segments of a channeled member are of substantially the same composition, shape, cross sectional area, and have substantially the same total number of passages and the same number of passages per unit cross-sectional area.

The internal volume of reactor 50 also includes a combustion zone, e.g., between terminal segments of the first and second channeled members. Although combustion zone can occupy less than all of the region between apertures 5 and 11 of the first and second channeled members, it is within the scope of the invention for the combustion zone to include all of the reactor's internal volume between apertures 5 and 11, e.g., the entire length L shown in FIG. 1. Typically, the combustion zone is centered in the region between apertures 11 and 5, e.g., with $L_2$ being substantially equal to $L_4$. As may be appreciated, the combustion zone occupies a region of reactor 50's internal volume during $t_H$ that is within the pyrolysis zone during $t_P$. However, since in the aspects illustrated in FIG. 1, a heating mode is not carried out at the same time as a pyrolysis mode, appreciable combustion does not occur in the combustion zone during pyrolysis and appreciable pyrolysis does not occur in the pyrolysis zone during heating.

The combustion zone is typically configured for (i) mixing the fuel and a portion of the oxidant during heating mode for efficient combustion, (ii) increasing distribution uniformity over third zone's internal cross sectional area of the combustion products, unreacted oxidant, and optionally unreacted fuel, and (iii) lessening undesirable pressure-drop effects during pyrolysis mode. The combustion zone can be a region within the internal volume of reactor 50, e.g., an open volume having a length L and substantially constant circular cross section of diameter D and cross sectional area A (not shown). As may be appreciated, an open volume having an appropriate L: A ratio will provide at least some mixing and distribution during heating mode without creating too great a pressure drop during pyrolysis mode. More typically, since it provides improved mixing and distribution and allows a lesser overall length for the combustion zone, the combustion zone includes at least one mixer-distributor apparatus 10. The mixer-distributor, which can be a channeled member in the form of a relatively thin plate having one or more orifices effective for carrying out the mixing and distribution of the heating mixture during heating mode. Generally, the orifices have sufficient cross sectional area to prevent an undesirably large pressure drop during pyrolysis mode. Conventional mixer-distributors can be used, such as those described in U.S. Patent Application Publication No. 2013-0157205 A1 and U.S. Pat. No. 7,815,873 (incorporated by reference herein in their entireties), but the invention is not limited thereto. In certain aspects, refractory components of the mixer-distributor comprise the same refractory as is used in the first channeled member. In other aspects, the mixer-distributor can be the sole channeled member in the reactor which comprises at least in part one or more of the first, second and third ceramics. Optionally, the combustion zone contains at least one selective combustion catalyst. Suitable selective combustion catalysts are described in U.S. Pat. No. 8,754,276, but the invention is not limited thereto. When used, a fixed bed of the selective combustion catalyst can be included as a component of the mixer-distributor, e.g., with one or more of the mixer-distributor's plate members serving as a catalyst support. When used, the mixer-distributor 10 can be located at any location within the combustion zone. Typically, however, it is located approximately mid-way between apertures 11 and 5. In certain aspects, however, such as those where the amount of coke deposits in channeled member 1 exceed that of channeled member 7, the combustion zone is shifted downstream (with respect to heating mixture flow) toward channeled member 1. The amount of shift is typically ≤25% of L, e.g., ≤20%, such as ≤10%.

The sum of lengths $L_1$, L, and $L_3$ is typically ≥90% of the total length of reactor 50 (≥0.9*$L_R$), e.g., as measured between openings 51 and 52. Since it is desirable to direct fuel and oxidant flows into appropriate passages of channeled member 7 during heating mode and to direct pyrolysis feed flow into appropriate passages of channeled member 1 during pyrolysis mode, it is typically desired to limit the internal volume between aperture 9 and opening 52 and between aperture 3 and opening 51, to that needed for convenient reactor assembly and to prevent component interference as might otherwise occur from thermal expansion during use. The pyrolysis zone, which generally encompasses all of region L, a segment of $L_1$, and a segment of $L_3$, is typically ≥10% of the total length of reactor 50, e.g., ≥15%, such as ≥20%. It is also typical for the pyrolysis zone to encompass ≤80% of the total length of reactor 50, e.g., to leave sufficient internal volume of channeled member 1 for pre-heating the pyrolysis feed and sufficient internal volume of channeled member 7 for quenching the pyrolysis product, e.g., ≤60%, such as ≤40%. In certain aspects, the pyrolysis zone has a length in the range of from 10% to 60% of the total length of the reactor, e.g., in the range of from 20% to 40%. The combustion zone's length L is typically ≤50% of that of the length of the pyrolysis zone, e.g., ≤40%, such as ≤30%, or ≤20%.

Values for L, $L_1$, $L_2$, $L_3$, $L_4$, and D generally depend on the pyrolysis feed used and the rate at which it is conducted into the reactor, the fuel and oxidant compositions, and the rate at which these are conducted into the reactor, etc. Although larger and smaller reactors are within the scope of the invention, (i) D is typically ≥1 cm. e.g., in the range of from about 1 cm to 10 m, such as 0.1 m to 7.5 m, (ii) $L_R$ is typically ≥1 cm, e.g., in the range of from about 1 cm to 20 m, such as 0.1 m to 7.5 m, (iii) L is typically ≤25% of $L_R$, e.g., ≤10%, (iv) $L_1$ is typically ≥35% of $L_R$ e.g., ≥45%, (v) $L_3$ is typically ≥35% of $L_R$, e.g., ≥45%, $L_3$ being optionally of substantially the same size and shape as $L_1$, and (vi) $L_2$ is typically within about +/−25% of $L_4$, e.g., +/−10%, such as +/−5%.

In certain aspects (not shown) at least a portion of the fuel-oxidant combustion is carried out in a location other than within the internal volume of reactor 50. For example, fuel combustion can be carried out at a location external to reactor 50, with the combustion products, unreacted oxidant, and optionally unreacted fuel being conveyed to the vicinity of the pyrolysis zone for (i) heating the pyrolysis zone to provide a desired temperature profile for efficiently carrying out the pyrolysis and (ii) combusting catalyst coke deposits with at least a portion of the unreacted oxidant.

In aspects illustrated schematically in FIG. 1, reactor 50 is heated during heating mode by conveying a heating mixture 19 comprising fuel and oxidant through opening 52, through aperture 9 of channeled member 7, and out of aperture 11 toward the combustion zone, which contains mixer-distributor 10. Typically, the fuel and oxidant are conveyed separately through different channels of channeled member 7 from aperture 9 toward aperture 11, and are combined to form the heating mixture downstream (with respect to fuel/oxidant flow) of channeled member 7. Typically fuel and oxidant are heated by a transfer of heat from channeled member 7 as the fuel and oxidant flow through the channels of channeled member 7. Combustion of the fuel and oxidant produces a combustion product. Combustion product, any un-combusted oxidant, and any un-combusted fuel enter aperture 5. When there is un-combusted oxidant in channeled member 1, this can react with coke deposits and any un-combusted fuel to produce additional combustion product. An aggregated combustion product 45 is conducted out of aperture 3 and away from the reactor via opening 51.

The aggregate combustion product typically comprises the combustion product produced in combustion zone 10; additional combustion product, typically from combustion of coke in passages of channeled member 1; and any unreacted fuel and/or any unreacted oxidant. Reactor 50 is switched from heating mode to pyrolysis mode after achieving the desired reactor temperature profile.

Continuing with reference to FIG. 1, a pyrolysis feed 15 is conducted into reactor 50 during pyrolysis mode via opening 51. The pyrolysis feed is preheated in an upstream segment of channeled member 1 and is typically pyrolysed in (i) a downstream segment of channeled member 1, and optionally also in (ii) the region between channeled member 1 and channeled member 7 and (iii) in an upstream segment of channeled member 7, upstream and downstream now being with respect to the flow of feed and pyrolysis product. A volatile portion 49 (typically gaseous) of the pyrolysis product is cooled in a downstream segment of channeled member 7, and exits channeled member 7 via aperture 9, and exits reactor 50 via opening 52. A non-volatile portion of the pyrolysis product remains in the reactor, typically as coke deposits. Accumulation of coke deposits in reactor 50 is lessened by combusting deposited coke during heating mode.

Heating mode is carried out for a time interval of duration ti to achieve a desired temperature profile in the internal volume of reactor 50 for the start of pyrolysis mode, primarily by fuel-oxidant combustion in combustion zone 10, coke-oxidant combustion in passages of channeled members 1 and 7, and optionally additional fuel-oxidant combustion in internal passages of channeled member 1 and (less typically) channeled member 7. Pyrolysis mode is carried out for a time interval of duration $t_P$. Pyrolysis is on-average endothermic, and, consequently, the bulk gas temperature profile of reactor 50 is transformed over the course of time interval $t_P$ to a profile that is not appropriate for efficient pyrolysis. Reactor 50 is then switched from pyrolysis mode to heating mode to reheat the reactor, so that the desired bulk gas temperature profile is exhibited at the start of a following pyrolysis mode. Typically, at least one flow controller which includes valve means (e.g., a plurality of valves) is provided to (i) establish forward flows of the pyrolysis feed and the pyrolysis product during pyrolysis mode for a time duration $t_P$ and (ii) establish reverse flows of the fuel, the oxidant, and the combustion product during heating mode for a time duration $t_H$.

Pyrolysis mode and heating mode are typically repeated in sequence, for semi-continuous or continuous operation. Intervening steps between successive pyrolysis and heating modes, e.g., one or more steps for admitting a forward or reverse flow of sweep gas to the reverse-flow reactor, can be carried out between pyrolysis mode and heating mode operation, and vice versa. Continuous or semi-continuous operation can be characterized by a "cycle time", which constitutes the time duration from the start of a pyrolysis mode to the start of the next pyrolysis mode in the sequence, and includes the time duration of heating mode(s) and any intervening steps (when used). Cycle time can be substantially constant over a plurality of repeated cycles, but this is not required. The invention is typically practiced with relatively short cycle times compared to that of conventional processes (e.g., steam cracking) for pyrolysing similar feed hydrocarbon at a peak pyrolysis temperature S 1200° C. For example, cycle time can be ≤60 seconds, e.g., ≤30 seconds, such as ≤15 seconds, or ≤5 seconds. Typically, cycle time is in the range of from 2 seconds to 60 seconds. e.g., 3 second to 30 seconds, such as 4 second to 30 seconds. When (i) the pyrolysis feed is introduced into the reactor in a direction that is substantially opposite to the direction of fuel and oxidant flow and/or (ii) when the flow of pyrolysis product away from the reactor is substantially opposite to the direction of combustion product flow, the reactor is called a reverse-flow reactor.

Certain aspects of heating mode operation, during which reactor 50 is preheated for initial pyrolysis mode operation, or reheated for continued pyrolysis mode operation, will now be described in more detail. The invention is not limited to these aspects, and this description is not meant to foreclose other ways to operate a heating mode.

Representative Heating Mode Conditions

Operating conditions during heating mode are selected to accomplish (i) reheating the pyrolysis zone to establish a temperature profile in the reactor corresponding to the desired bulk gas temperature profile at the start of a following pyrolysis mode and (ii) removing sufficient coke deposits from within the reactor's internal volume, which would otherwise lead to an increase in reactor pressure drop. When it is desired to quench the pyrolysis product within the reactor, heating mode optionally includes cooling channeled member within the reactor at a location that is both upstream (with respect to fuel-oxidant flow) of the combustion zone and downstream (with respect to the flow of pyrolysis product) of the pyrolysis zone.

Combustion is carried out during heating mode by reacting fuel and oxidant, e.g., fuel and oxidant contained in a heating mixture. The fuel and oxidant can be the same as those disclosed in U.S. Pat. No. 7,943,808. Optionally, the fuel is derived from, comprises, consists essentially of, or consists of one or more of hydrogen, CO, methane, methane containing streams, such as coal bed methane, biogas, associated gas, natural gas and mixtures or components thereof, etc. The fuel typically comprises one or more of molecular hydrogen, synthesis gas (mixtures of CO and $H_2$), and hydrocarbon, such as ≥10.0 wt. % hydrocarbon, or ≥50.0 wt. % hydrocarbon, or ≥90.0 wt. % hydrocarbon. Although the fuel can be of substantially the same composition as the pyrolysis feed, this is not required. The oxidant is typically one or more of molecular oxygen, ozone, and air, including molecular oxygen in air. Those skilled in the art will appreciate that feed flow rate will depend on factors such as feed composition, reactor volume, pyrolysis conditions, etc. Accordingly, the invention can be carried out over a very wide range of heating mixture flow rates, e.g., at a flow rate≥0.001 kg/s, such as ≥0.1 kg/s, or ≥10 kg/s, or ≥100 kg/s, or more.

Once a fuel of the desired caloric content (heating value) has been selected, the amounts of fuel and oxidant to the reactor during heating mode can be specified in terms of the amount of oxidant needed for combusting the accumulated coke deposits ("$OC_a$") and the amount of oxidant ("$OC_b$") needed for the substantially stoichiometric combustion of the fuel. Typically, the oxidant supplied during heating mode is $Z \cdot (OC_a + OC_b)$, wherein Z is generally ≥0.5, e.g., ≥0.8, such as in the range of 0.5 to 5.0, or 0.5 to 3.0, or 0.8 to 3.0. The amounts $OC_a$ and $OC_b$ are on a molar basis. When Z>1.0, the excess oxidant can be utilized, e.g., for one or more of removing at least a portion of any accumulated coke deposits, moderating the reaction temperature during heating mode (as disclosed in U.S. Pat. No. 7,943,808), and conveying heat within the reactor from one zone to another. Generally, a first portion of the oxidant is combusted with the fuel in the combustion zone, and a second portion is combusted with accumulated coke deposits. Typically, the first portion comprises ≥50 wt. % of the total amount of oxidant supplied during heating mode, e.g., ≥75 wt. %, or ≥90 wt. %, with the second portion comprising at least 75 wt. % of the remainder of the total oxidant, e.g., ≥90 wt. %. It is also typical for oxidant flow rate and fuel flow rate to remain substantially constant for the duration of heating mode. These flow rates are selected to achieve the desired amount of combustion heating and the desired amount of coke removal during $t_H$. The invention is compatible with conventional methods for lessening coke accumulation in channeled members during heating mode, e.g., those described in U.S. Pat. No. 9,187,382, which is incorporated by reference in its entirety.

Other streams can be provided to the reactor during heating mode, e.g., one or more diluent streams can be provided, such as by addition to the heating mixture. When used, diluent can be provided with the oxidant and/or fuel. Suitable diluents (which can be a diluent mixture) include one or more of, e.g., oxygenate (water, carbon dioxide, etc.), non-combustible species, such as molecular nitrogen ($N_2$), and fuel impurities, such as hydrogen sulfide. For example, the oxidant can comprise 60.0 mole % to 95.0 mole % diluent and 5.0 mole % to 30.0 mole % molecular oxygen per mole of the oxidant, such as when the oxidant is air. Optionally, the oxidant has a mass ratio of diluent to molecular oxygen in the range of 0.5 to 20.0, e.g., in the range of 4.0 to 12.0.

In order to lessen or prevent the occurrence of a sharp temperature gradient in the bulk gas temperature profile at the start of pyrolysis mode and during the course of pyrolysis mode, it was expected that a relatively long-duration $t_H$ would be needed, e.g., a $t_H \geq 30$ seconds, or ≥50 seconds. Surprisingly, this is not the case: a $t_H \leq 27$ seconds is typically sufficient for reheating the reactor to achieve the desired bulk gas temperature profile at the start of pyrolysis mode, e.g., ≤25 second, such as ≤10 seconds, or ≤1 second, or ≤0.1 second. For example, $t_H$ can be in the range of from 0.01 second to 25 seconds, or 0.05 second to 10 seconds, or 0.05 second to 5 seconds, or 0.05 second to 1 second.

It was also expected that fuel-oxidant combustion should be distributed through the reactor's pyrolysis zone to achieve the desired non-constant bulk gas temperature profile in the pyrolysis zone (and particularly along channeled member 1) during $t_P$, and to lessen or prevent the occurrence of a sharp temperature gradient in the bulk gas temperature profile during $t_P$. Surprisingly, it has been found that this is not the case. The desired bulk gas temperature profile for pyrolysis mode is established during heating mode by carrying out fuel-oxidant combustion primarily in the central region of the reactor (e.g., a region of length L as shown in FIG. 1). While not wishing to be bound by any theory model, it is believed that concentrating combustion in the central region of the reactor leads to an improved reactor temperature profile compared to that which is achieved by distributed combustion for mainly two reasons. First, the greater fuel and oxidant flow rates needed to achieve the desired amount of combustion during $t_H$, and the resulting increased flow rate of combustion product, lead to a more favorable distribution of combustion heat within the reactor. Second, during heating mode the combination of radiative heat transfer to a channeled member proximate to the combustion zone and heat conduction within the channeled member sufficiently moderates the reactor temperature profile so as to broaden temperature gradients in the pyrolysis zone (e.g., gradients along the length of the reactor) that would otherwise be undesirably sharp.

Referring again to FIG. 1, an appropriate combustion zone length L can be achieved by conventional methods, e.g., by use of one or more mixer-distributors 10, use of a selective combustion catalyst, etc. For example, it has been found that even when mixer-distributors and selective combustion catalysts are not used, limiting Z to a value ≤5.0, e.g., ≤3.0, and especially <2.0, results in a combustion zone length L that is ≤50% of that of the length of the pyrolysis zone, e.g., ≤40%, such as ≤30%, or ≤20%.

After the reactor is sufficiently reheated to establish the reactor temperature profile desired at the start of pyrolysis, the reactor can be switched from heating mode to pyrolysis mode, typically by decreasing or terminating fuel and oxidant flow and commencing or increasing a flow of pyrolysis feed. Representative pyrolysis feeds will now be described in more detail. The invention is not limited to these pyrolysis feeds, and this description is not meant to foreclose the use of other pyrolysis feeds within the broader scope of the invention.

Representative Pyrolysis Feeds

The pyrolysis feed comprises $C_{2+}$ hydrocarbon, e.g., ≥1 wt. % of $C_{2+}$ hydrocarbon, such as ≥10 wt. %, or ≥25 wt. %, or ≥50 wt. %, or ≥75 wt. %, or ≥90 wt. %. Typically ≥90 wt. % of the remainder of the pyrolysis feed comprises diluent, e.g., one or more of methane, $CO_2$, water, etc. In certain aspects, the pyrolysis feed consists essentially of or even consists of $C_{2+}$ hydrocarbon. e.g., $C_2$-$C_9$ paraffinic hydrocarbon. The pyrolysis feed's hydrocarbon (the "feed hydrocarbon") generally includes any hydrocarbon compounds or mixture of hydrocarbon compounds that when subjected to the specified pyrolysis conditions produce the desired pyrolysis product. Suitable pyrolysis feeds include those disclosed in U.S. Patent Application Publication No. 2016-176781, which is incorporated by reference herein in its entirety. In certain aspects, particularly those aspects where the feed comprises ≥50 wt. % ethane (or propane, or a mixture of ethane and propane), e.g., ≥75 wt. %, such as ≥90 wt. %, conversion during pyrolysis is based on the amount of $C_{2+}$ hydrocarbon that is converted. In other aspects, e.g., those where the feed includes components such as (i) saturated $C_{4+}$ hydrocarbon and/or (ii) aromatic and/or non-aromatic cores having one or more substantially-saturated $C_{2+}$ side chains, the conversion is based on the aggregate amount of $C_{2+}$ hydrocarbon components converted, including such substantially saturated side chains as may be converted.

Although the feed hydrocarbon typically includes $C_{2+}$ compounds which contain hydrogen and carbon only, feed hydrocarbon can contain compounds having covalently-bound and/or non-covalently-bound heteroatoms. When present in the feed hydrocarbon, the amount of such heteroatom-containing hydrocarbon compounds is typically ≤10 wt. % based on the weight of the feed's hydrocarbon. Feed hydrocarbon that is substantially-free of non-aliphatic hydrocarbon is within the scope of the invention, as is feed hydrocarbon that is substantially free of aromatic hydrocarbon and/or substantially free of olefinic hydrocarbon, particularly $C_2$-$C_5$ olefin. Substantially-free in this context means <1 wt. % based on the weight of the feed hydrocarbon, such as ≤0.1 wt. %, or ≤0.01 wt. %, or ≤0.001 wt. %.

The feed hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include a recycled portion of the pyrolysis product. Such recycle, when used, can include, e.g., methane, molecular hydrogen, and $C_{2+}$ hydrocarbon, typically $C_2$ to $C_5$.

The feed hydrocarbon can include one or more of ethane, propane, butanes, saturated and unsaturated $C_6$ hydrocarbon, including those derived from one or more of Fischer-Tropsch synthesis products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$-residue admixture, naphtha-residue admixture, cracked feed, coker distillate streams, and hydrocarbon streams derived from plant or animal matter. The feed hydrocarbon can comprise volatile and non-volatile hydrocarbon, as described in U.S. Patent Application Publication No. 2016-176781. Those skilled in the art will appreciate that feed flow rate will depend on factors such as feed composition, reactor volume, pyrolysis conditions, etc. Accordingly, the invention can be carried out over a very wide range of feed flow rates, e.g., at a flow rate≥0.001 kg/s, such as ≥0.1 kg/s, or ≥10 kg/s, or ≥100 kg/s, or more.

Although the invention is not limited thereto, the specified process can be used for upgrading relatively refractory light (e.g., $C_2$-$C_5$) paraffinic hydrocarbon, such as ethane. Accordingly, the feed hydrocarbon can comprise ethane in an amount ≥1 wt. %, e.g., ≥5 wt. %, such as ≥10 wt. %. Suitable feeds include those comprising >50 wt. % ethane, such as ≥75 wt. %, or ≥90 wt. %, or ≥95 wt. %. For example, the feed can comprise an amount of ethane in the range of from 1 wt. % to 99 wt. %, such as 5 wt. % to 95 wt. %, or 10 wt. % to 90 wt. %. One representative feed hydrocarbon comprises (i) ≥10 wt. % ethane, or ≥50 wt. %, or ≥90 wt. %, such as in the range of from 10 wt. % to 99.5 wt. % ethane, with ≥95 wt. % of the balance of the feed hydrocarbon comprising one or more of methane, propane, and butanes. In other aspects, the feed comprises ≥90 wt. % of (i) ethane and/or (ii) propane. The light paraffinic hydrocarbon can be provided from any convenient source, e.g., from synthetic and/or natural sources. Light paraffinic hydrocarbon (e.g., ethane) can be provided from petroleum or petrochemical processes and/or sources of geological origin, e.g., natural gas. In particular aspects, the pyrolysis feed comprises ≥90 wt. % of (i) ethane and/or (ii) propane.

The pyrolysis feed optionally includes diluent, typically comprising compositions that are essentially non-reactive under the specified pyrolysis conditions, such as one or more of methane, water (e.g., steam), hydrogen, nitrogen and the noble gases, such as helium, neon and argon. Diluent present in the pyrolysis feed's source (e.g., methane and/or $CO_2$ present in natural gas) and diluent added to the pyrolysis feed are within the scope of the invention. Diluent, when present, is typically included in the pyrolysis feed in an amount ≤60 wt. % based on the weight of the feed, e.g., ≤50 wt. %, such as ≤40 wt. %, or ≤30 wt. %, or ≤20 wt. %, or ≤10 wt. %, or in the range of from 1 wt. % to 50 wt. %. Diluent is also suitable for use as a sweep gas, e.g., for (i) removing at least a portion of any deposits in the reactor after the pyrolysis mode and/or after heating mode and/or (ii) adjusting the reactor's temperature profile—heat carried by the sweep gas from warmer regions of the reactor for transfer to cooler regions will increase the temperature of the cooler regions and further lessen or prevent sharp gradients in the reactor temperature profile.

A flow of the pyrolysis feed is conducted to the pyrolysis reactor during pyrolysis mode, typically in a reverse-flow direction, e.g., one that is opposed to that of oxidant flow. During pyrolysis mode, at least a portion of the feed hydrocarbon is pyrolysed to produce a desired pyrolysis product. Certain pyrolysis conditions that are useful for pyrolysing the specified pyrolysis feeds will now be described in more detail. The invention is not limited to these pyrolysis conditions, and this description is not meant to foreclose the use of other pyrolysis conditions within the broader scope of the invention.

Representative Pyrolysis Mode Conditions

When heating mode is carried out under the specified conditions, the bulk gas temperature profile at the start of pyrolysis mode continuously varies over the length of the pyrolysis zone, and typically over the entire length of channeled member 1. Utilizing a first channeled member having an OFA≤55% in a pyrolysis reactor operating under the specified pyrolysis conditions has been found to result in a number of favorable features, e.g., a feed conversion that is typically ≥50 wt. % and desirable olefin yields, typically without excessive coke yield. Although $T_p$ decreases during the course of the pyrolysis, its position along the length of the pyrolysis zone and the general shape of the bulk gas temperature profile typically remain substantially the same during $t_P$. More particularly, utilizing a first channeled member having an OFA in the specified range results in a decrease in $T_p$ that is ≤100° C. during $t_P$, e.g., ≤75° C., such as ≤50° C., or ≤25° C., or ≤10° C., or ≤5° C., for a wide range of pyrolysis conditions and a wide selection of pyrolysis feeds. In certain aspects, e.g., those where $T_p$ is located downstream of the first channeled member, the bulk gas temperature proximate to the downstream end of the first channeled member decreases by ≤100° C. during the course of the pyrolysis, e.g., ≤75° C., such as ≤50° C., or ≤25° C., or ≤10° C., or ≤5° C. Regions of substantially-constant temperature along the length of the pyrolysis zone (and typically along the length of channeled member 1) are avoided. Sharp gradients in the bulk gas temperature profile within the pyrolysis zone (and typically along the length of channeled member 1) are also substantially avoided. Although high-severity pyrolysis conditions can be used, it is typical to use low severity conditions.

When OFA is in the specified range, $T_p$ and/or $T_{av}$ remain within 100° C. of their values at the start of the pyrolysis even when $t_P$ is of relatively long duration, e.g., ≥1 second, such as ≥2 seconds, or ≥5 seconds, or ≥10 seconds, or ≥20 seconds, or ≥30 seconds, or even ≥1 minute or more. For example, $t_P$ can be in the range of from 1 second to 30 seconds, e.g., 2 seconds to 15 seconds, such as 2 seconds to 10 seconds. Conventional methods can be used to achieve these ranges of $t_P$, e.g., using one or more poppet valves and/or hydrodynamic valving, but the invention is not limited thereto. The bulk gas temperature profile typically maintains a substantially constant shape (although decreasing in magnitude) during these relatively long $t_P$ values. Using a $t_P$≥2 seconds and the specified OFA decreases the occurrence of pyrolysis zone segments having a substantially-constant bulk gas temperature profile. Using these $t_P$ values and the specified OFA also substantially prevents relatively sharp temperature gradients in the pyrolysis zone.

For example, at any time during the pyrolysis variations in the bulk gas temperature are typically ≤140° C. within any pyrolysis zone segment having a length≤10% of $l_C$, e.g., ≤100° C., such as ≤50° C. Using these $t_P$ values and the specified OFA typically limits temperature variations to ≤75° C. within any segment of channeled member 1 that has a length≤10% of $l_B$, e.g., ≤50° C., such as ≤25° C.

The pyrolysis conditions in the pyrolysis zone during $t_P$ generally include $T_p$≤1400° C., $T_{av}$≤1200° C. and an average total pressure≥0 psig. Gas residence time in the pyrolysis zone (e.g., feed residence time when the feed is substantially non-liquid during the pyrolysis) is generally ≤0.4 seconds to decrease the conversion to coke of desired products such as light olefin. Typically, the pyrolysis conditions include $T_p$≤1200° C., e.g., ≤1100° C., such as ≤1000° C. or in the range of from 1000° C. to 1400° C.; $T_{av}$≤1100° C., e.g., ≤1000° C., such as ≤900° C., or in the range of from 600° C. to 1200° C., or 900° C. to 1100° C., or 925° C. to 1075° C.; and a feed hydrocarbon partial pressure≥7 psia (48 kPa), or ≥10 psia (69 kPa), or ≥20 psia (138 kPa), or ≥30 psia (207 kPa). The average total pressure is typically ≥5 psig (34 kPag), or ≥15 psig (103 kPag), or ≥40 psig (276 kPag), or ≥80 psig (552 kPag), or ≥120 psig (827 kPag). Particularly when the pyrolysis feed includes diluent, the average total pressure can be ≥150 psig (1034 kPag), or ≥300 psig (2068 kPag), or ≥500 psig (3447 kPag). Total gas residence time in the pyrolysis zone is typically ≤0.2 second; preferably ≤0.15 second or ≤0.1 second; or in the range of 0.001 second to 0.4 second, or in the range of 0.01 second to 0.4 second, or in the range of 0.01 second to 0.2 second. For example, the pyrolysis feed can be passed through channeled member 1 at a total gas residence time at a bulk gas temperature≥800° C. that is ≤0.100 second, such as ≤0.060 second, such as ≤0.040 second, or in the range of 0.001 second to 0.100 second, or in the range of 0.002 second to 0.060 second, or in the range of 0.002 second to 0.040 second. When utilizing a first channeled member having an OFA in the specified range, these conditions have been observed to decrease $T_p$ and/or $T_{av}$ by ≤100° C., e.g., ≤75° C., such as ≤50° C., or ≤25° C., or ≤10° C., or ≤5° C., for a $t_P$≥1 second, e.g., ≥2 seconds, such as ≥5 seconds, or ≥10 seconds, or ≥20 seconds, or ≥30 seconds, or even ≥1 minute or more. In particular aspects, $t_P$ and $t_H$ are both ≥2 sec., feed hydrocarbon conversion is ≥50 wt. %, gas residence time in the pyrolysis zone is ≤0.5 second, and total pressure is ≥0 psig.

Smaller values of OFA, which lead to a smaller decrease in $T_p$ and $T_{av}$ during $t_P$, are typically desired at relatively large values of $T_p$, e.g., ≥1000° C., such as ≥1200° C., or ≥1300° C. Decreasing variations in $T_p$ and $T_{av}$ during $t_P$ at relatively high pyrolysis temperatures has been found to moderate variations in the yield of less desirable pyrolysis products such as acetylene and coke as would otherwise occur during a commercially-reasonable $t_P$ (e.g., ≥2 seconds). This in turn leads to a simplification of olefin purification and recovery facilities. For example, when $T_{av}$ exceeds 900° C., it is beneficial for the channeled member to have an OFA of ≤45%, and for $\Delta T_p$ and/or $\Delta T_{av}$ to be ≤50° C. When $T_{av}$ exceeds 1000° C., it is beneficial for the channeled member to have an OFA of ≤35%, and for $\Delta T_p$ and/or $\Delta T_{av}$ to be ≤40° C. When $T_{av}$ exceeds 1100° C., it is beneficial for the channeled member to have an OFA of ≤25%, and for $\Delta T_p$ and/or $\Delta T_{av}$ to be ≤20° C. Stated another way, when $T_P$ exceeds 1000° C., it is beneficial for $\Delta T_p$ and/or $\Delta T_{av}$ to be ≤50° C., when $T_P$ exceeds 1100° C., it is beneficial for $\Delta T_p$ and/or $\Delta T_{av}$ to be ≤40° C., and when $T_P$ exceeds 1200° C., it is beneficial for $\Delta T_p$ and/or $\Delta T_{av}$ to be ≤20° C.

Thermal profiles resulting from using the specified regenerative reactor having a thermal mass of the specified OFA for a pyrolysis mode having the specified time duration $t_P$ will now be described in more detail with respect to FIGS. 2 and 3. In FIGS. 1-3, components and streams performing similar functions have the same index number. As shown in the figures, $\Delta T_p$ is a positive number corresponding to the change in $T_p$ during $t_P$. Although FIGS. 2 and 3 illustrate aspects where $T_p$ is located within shaded region 14 of channeled member 1, in other aspects $T_p$ is located downstream (respecting pyrolysis feed flow) of channeled member 1.

FIG. 2 schematically shows a representative regenerative reverse-flow reactor, similar to that shown in FIG. 1, and representative gas temperature profiles during pyrolysis. The solid line represents the bulk gas temperature profile at the start of $t_P$, and the dashed line represents the bulk gas temperature profile at the end of $t_P$. At the start of $t_P$, the flow of combustion mixture 19 is curtailed a flow of pyrolysis feed 15 is established. The reactor's pyrolysis zone at the start of $t_P$ encompasses the region between apertures 5 and 11, the shaded region 16 of channeled member 7, and the shaded region 14 of channeled member 1. Particularly at relatively large flow rates of fuel and/or oxidant during heating mode, and/or when $t_H$ is of relatively long duration, the peak gas temperature $T_p$ during $t_P$ can be displaced away from the aperture 11, toward aperture 5 or beyond. In such aspects, the length of the pyrolysis zone's downstream segment $l_B$ is less than that of the upstream segment $l_A$, e.g., at least 10% less, such as at least 25% less, or at least 50% less. The total length of the pyrolysis zone $l_C$ is the sum of $l_A$ and $l_B$. Typically, $l_C$ is in the range of from 10% to 50% of the total length of reactor 50, e.g., in the range of 20% to 40%. For example, $l_C$ can be in the range of from 20% to 40% of $L_1+L_2+L_3+L_4$ (FIG. 2). The locations of the terminal ends of $l_A$ and $l_B$ (the locations where the first and second heat transfer zones abut the pyrolysis zone during pyrolysis mode) are determined by $T_{MIN}$.

In the aspect of FIG. 3, a mixer-distributor 10 is located within the combustion zone, and the bulk gas temperature profile at the start of pyrolysis mode (profile PR$_3$) exhibits at two local maxima. Profile PR$_4$, which represents the bulk gas temperature profile at the end $t_P$, also exhibits two local maxima and is substantially congruent with PR$_3$. While not wishing to be bound by any theory or model, it is believed that the bi-modal bulk gas temperature profile results from heat radiated from the mixer distributor during heating mode toward channeled members 1 and 7. Since the end of the mixer-distributor opposite aperture 5 achieves a greater temperature than the end facing aperture 11 during heating mode, and since radiative heating is a relatively short-range phenomena (the inverse-square law applies), channeled member 1 is heated more than channeled member 7. The resultant bulk gas temperature profile PR$_3$ at the start of pyrolysis mode is therefore believed to be a substantially linear combination of bulk gas temperature profile PR$_1$, which is related to the heating of channeled member 7, and bulk gas temperature profile PR$_2$, which is related to the heating of channeled member 1. Greater fuel-oxidant flow rates during heating mode lead to additional heating of channeled member 1, e.g., by convective heat transfer from the combustion product, which displaces the peak temperature of profile PR$_2$ toward (or even into) shaded region 14. The maximum gas temperature of profile PR$_1$ is typically 20% to 70% of the maximum gas temperature of profile PR$_2$, such as 30% to 70%.

In aspects such as those illustrated in FIGS. 2 and 3, the pyrolysis conditions include a bulk gas temperature profile during pyrolysis (i.e., the profile of the pyrolysis bulk gas temperature) which at the start of $t_P$ increases substantially monotonically from a first temperature ($T_1$) proximate to aperture 3 of thermal mass 1 to temperature $T_{MIN}$ proximate to a location (the reference location) where the first heat transfer zone abuts the pyrolysis zone, e.g., reference location $R_1$ at the start of $t_P$ and reference location $R_2$ at the end of $t_P$. The peak gas temperature $T_p$ is greater than $T_mIN$ during $t_P$. $T_p-T_{MIN}$ at the start of pyrolysis is typically in the range of from 10° C. to 400° C., or 25° C. to 300° C., or 50° C. to 200° C. $T_{av}$ is typically $\geq T_{MIN}+10°$ C. at the start of $t_P$. For example, $T_{av}-T_{MIN}$ at the start of pyrolysis is typically in the range of from 5° C. to 200° C., or 10° C. to 150° C., or in a range of from 20° C. to 100° C., or from 25° C. to 75° C. Typically, the position of $T_p$ within the pyrolysis zone remains substantially constant during the pyrolysis. Substantially constant in this context means that the location of $T_p$ changes during pyrolysis mode from its initial position by $\leq +/-20\%$ of $l_c$, e.g., $\leq +/-15\%$, such as $\leq +/-10\%$, or typically $\leq +/-5\%$. Unlike $T_p$, the reference location typically varies in position during $t_P$. $T_1$ is typically less than $T_{IN}$ during $t_P$, in other words, at least a segment of first thermal mass 1 is included in the first heat transfer zone. The value of $T_{MIN}$ depends on several factors, e.g., the choice of feed and pyrolysis process conditions such as pressure and residence time. For feeds comprising light hydrocarbon, e.g., one or more $C_2-C_5$ paraffin, $T_{MIN}$ is typically $\leq 1400°$ C. e.g., $\leq 1300°$ C., such as $\leq 1200°$ C., or $\leq 1100°$ C., or $\leq 1000°$ C. For example, $T_{MIN}$ is typically in the range of from 700° C. to 1200° C., e.g., 975° C. to 1100° C., and $T_p$ is typically $\geq 1150°$ C. $T_{MIN}-T_1$ at the start of pyrolysis is typically in the range of from 10° C. to 400° C., or 25° C. to 300° C., or 50° C. to 200° C. In particular aspects utilizing a feed comprising ethane and/or propane, the pyrolysis conditions at the start of $t_P$ typically include $T_1 \leq 900°$ C., e.g., $\leq 750°$ C., such as $\leq 500°$ C., or $\leq 400°$ C., or in the range of from 350° C. to 800° C.

At the start of $t_P$, feed conversion typically exhibits a profile (not shown in FIGS. 2 and 3) which increases from a first conversion ($X_1$) at reference location $R_1$ positioned between the first and second apertures to a second conversion ($X_2$) proximate to aperture 5, wherein $X_i$ is in the range of from 25% to 85%, and $X_2$ is in the range of from 65% to 98%. Reference location $R_1$ is typically proximate to the location where the terminal the end of the pyrolysis zone abuts the first heat transfer zone at the start of $t_P$. The peak gas temperature decreases during $t_P$, but the bulk gas temperature profile typically maintains substantially the same shape as shown. Although the bulk gas temperature profile (within the pyrolysis zone) at the start of $t_P$ is typically substantially congruent with that at the end of $t_P$, the location in the pyrolysis zone at which conversion $X_1$ is achieved translates during $t_P$ from $R_i$ toward aperture 5 to reference position $R_2$ at the end of $t_P$. In particular aspects where the feed comprises ethane and/or propane, the process can include one or more of (i) $X_I$ in the range of from 25% to 60%, (ii) the bulk gas temperature proximate to aperture 5 is in the range of from 1025° C. to 1075° C., (iii) $X_2$ in the range of from 85% to 98%, (iv) $T_{MIN}$ in the range of from 900° C. to 1000° C., and (v) the reference location $R_1$ is positioned within $0.2*L_1$ and $0.4*L_1$ of aperture 5. More particularly, conditions at the start of the pyrolysis can include (i) an acetylene selectivity in a range of from 0% to 1% at the reference location, which acetylene selectivity increases, e.g., monotonically, to a range of 5% to 10% at the second aperture, (ii) an ethylene selectivity in a range of from 85% to 95% at the reference location, which ethylene selectivity decreases, e.g., monotonically, to a range of 70% to 85% at the second aperture, (iii) a propylene selectivity in a range of from 0.7% to 0.9% at the reference location, which propylene selectivity varies monotonically or non-monotonically to a range of 0.4% to 0.6% at the second aperture, and (iv) a benzene selectivity (corresponding to selectivity for coke and coke precursors) in a range of from 0.005% to 1.5% at the reference location, which butadiene selectivity increases, e.g., monotonically, to a range of 4% to 5% at the second aperture.

By modulating bulk gas temperature over the length of the pyrolysis zone during pyrolysis mode, the pyrolysis product conducted away from the reactor comprises a range of desired hydrocarbon products, including a desirable range of $C_2-C_5$ olefin. Typically, one or more of the desired hydrocarbon compounds is separated from the pyrolysis product, e.g., for storage and/or further processing. For example, one or more of ethylene, propylene, butadiene butenes, etc. can be separated from the pyrolysis product. e.g., for recovery and use in producing products such as fuels and fuel additives, oxygenates, polymer, etc. Molecular hydrogen and methane can be separated and recovered from the pyrolysis product, e.g., as a tail gas. Light paraffinic hydrocarbon can be separated recovered, e.g., for use as a fuel, such as a fuel for heating mode. Conventional separations and recovery methods can be used, e.g., those described in U.S. Patent Application Publication No. 2016-176781, but the invention is not limited thereto. Since OFA and/or $t_P$ are selected so that $T_p$ or $T_{av}$ (and typically both) decrease by $\leq 100°$ C. during the course of the pyrolysis, e.g., $\leq 75°$ C., such as $\leq 50°$ C., or $\leq 25°$ C., or $\leq 10°$ C., or $\leq 5°$ C., yields of these desired products typically do not vary appreciably as a function of time during the course of the pyrolysis, leading to a considerable simplification of product recovery systems over conventional processes.

Certain representative pyrolysis products will now be described in more detail. The invention is not limited to these products, and this description is not meant to foreclose the production of other pyrolysis products within the broader scope of the invention.

Representative Pyrolysis Products

In certain aspects, the pyrolysis product conducted away from the reactor is primarily gaseous and comprises molecular hydrogen; methane; ethane; ethylene; propane; propylene; butanes; butenes; butadiene; $C_5$ hydrocarbon, including normal, iso, and cyclo $C_5$ olefin and paraffin, and $C_{6+}$ hydrocarbon, including aromatics and normal, iso, and cyclo $C_{6+}$ olefin and paraffin. For example, when utilizing one representative pyrolysis feed comprising light paraffinic hydrocarbon and representative heating mode and pyrolysis mode conditions, the pyrolysis product can comprise 2 wt. % to 10 wt. % methane, 50 wt. % to 95 wt. % ethylene, 0.2 wt. % to 1 wt. % propylene, 0.1 wt. % to 5 wt. % butadiene, and up to about 3 wt. % benzene, based on the weight of the pyrolysis product. As may be appreciated, these very desirable compositional ranges for the identified hydrocarbon compounds are achieved not only at the start of pyrolysis mode, but during the duration of $t_P$. This stands in sharp contrast to conventional processes operating at a gas temperatures $\leq 1200°$ C., such as steam cracking, since these operate with little temperature variation in the pyrolysis zone, and produce a pyrolysis product having very narrow compositional ranges for the desired hydrocarbon compounds.

Example

In this prophetic example, a pyrolysis feed consisting essentially of ethane is exposed to the specified pyrolysis conditions in a representative reverse-flow reactor configured to be similar to the one illustrated in FIG. 2. Channeled member 1 is an alumina honeycomb having an OFA of 0.55 and a Cp of 0.13 kj kg$^{-1o}$ K$^{-1}$. The alumina has a mass density of about 3900 kg/m$^3$. $T_{av}$ is about 990° C. at the start of pyrolysis mode, and is achieved at about midway along the reactor's length (proximate to the midpoint of $l_C$). Gas residence time during pyrolysis mode is 0.2 seconds. Average total pressure doing the pyrolysis is 2.4 bar (absolute). The pyrolysis is carried out for a time $t_P$ of 20 seconds.

Figure 4:
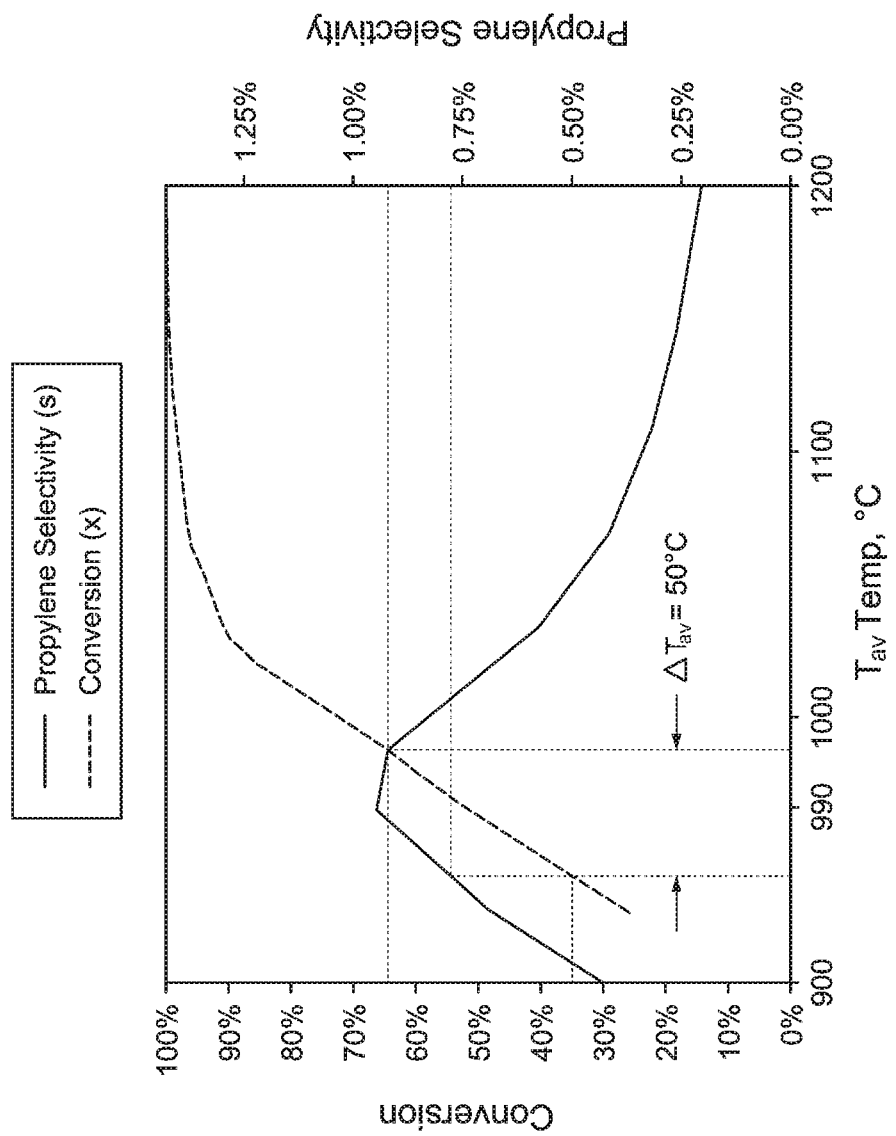
FIG. 4 shows the variation of conversion (dashed line) and propylene selectivity (solid line) as a function of $T_{av}$ under the conditions specified in the Example.
Figure 5:
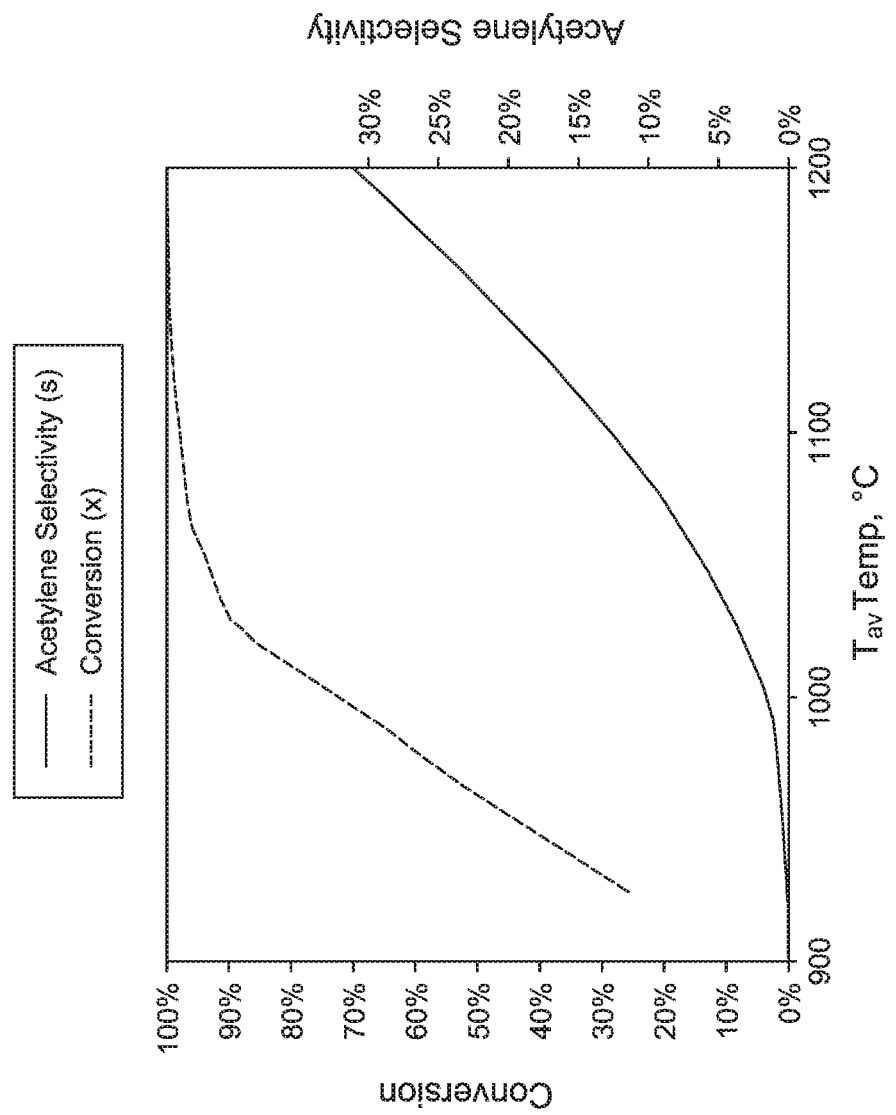
FIG. 5 shows the variation of conversion (dashed line) and acetylene selectivity (solid line) as a function of $T_{av}$ under the conditions specified in the Example.

The location of $T_P$ within the reactor is substantially constant during $t_P$, and $T_{av}$ at the end of pyrolysis mode is 940° C. Propylene yield (selectivity times conversion) does not vary appreciably over the indicated range of $\Delta T_{av}$, decreasing during $t_P$ from about 0.6 wt. % to about 0.3 wt. %. Since acetylene selectivity (FIG. 5) decreases slightly during $t_P$ (as does conversion), there is also a slight decrease in acetylene yield. Ethylene selectivity (not shown) increase slightly during $t_P$, resulting in little change in ethylene yield during $t_P$. Ethylene selectivity (not shown) increases during $t_P$, but this effect is partially offset by a commensurate decrease in conversion, resulting in an ethylene yield that does not vary appreciably during $t_P$. Accordingly, utilizing a first channeled member having an OFA≤55% results in a $\Delta T_{av}$ of ≤100° C., leading to ethylene and propylene yields which do not vary appreciably as a function of time during a $t_P$ that is of sufficient duration to be commercially achievable using conventional valving. Moreover, since there is little variation in acetylene yield during $t_P$, the separation of propylene from unsaturated $C_2$ compounds can be carried out efficiently without the need to include additional separation capacity. As can be seen in FIGS. 4 and 5, a lesser OFA is beneficial when the pyrolysis is carried out at a greater initial $T_{av}$, e.g., ≥1000° C., such as ≥1100° C., in order to provide a smaller $\Delta T_{av}$, which in turn lessens the variation in acetylene yield during $t_P$.

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all patentable features which reside herein, including all features which would be treated as equivalents thereof by those skilled in the relevant art. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of." "selected from the group of consisting of," or "is" preceding the recitation of the composition, component, or components, and vice versa.

We claim:

1. A reverse-flow reactor, comprising:
   (a) a first channeled member having open frontal area (OFA)≤55%, the first channeled member comprising at least one refractory and having opposed first and second apertures and at least one internal channel, wherein
      (i) the second aperture is separated from the first aperture by a first flow-path through the channel,
      (ii) the refractory includes one or more of a first ceramic comprising at least one compound represented by the formula $M_{n+1}AX_n$, a second ceramic comprising at least one compound represented by the formula $N_iB_j$, and a third ceramic comprising at least one compound represented by the formula $P_kQ_m$, and
      (iii) M is at least one element selected from Groups 3-6 of the Periodic Table, A is at least one element selected from Groups 13-15 of the Periodic Table; X is carbon and/or nitrogen; N is at least one element selected from Groups 4 and 5 of the Periodic Table; B is boron; P is at least one element selected from Groups 4-10 of the Periodic Table; Q is silicon and/or aluminum; n is 1, 2, or 3; i and k are each a positive integer; j is i+1 or i+2; and m is a positive integer that can be greater than k, less than k, or equal to k;
   (b) a second channeled member comprising at least one refractory and having opposed first and second apertures and at least one internal channel, the first and second apertures being separated by a second flow-path through the channel,
   (c) a reactor vessel having opposed first and second openings and an internal volume, wherein (i) the internal volume includes the first and second channeled members; (ii) the first opening is adjacent to the first aperture of the first channeled member and the second opening is adjacent to the second aperture of the second channeled member, and (iii) the first and second openings are in fluidic communication through the first and second flow-paths;
   (d) at least one feed conduit in fluidic communication with the first opening, at least one reaction product conduit in communication with the second opening, at least one fuel conduit in fluidic communication with the second opening, at least one oxidant conduit in fluidic communication with the second opening, and at least one combustion product conduit in fluidic communication with the first opening;
   (e) at least one flow controller for
      (i) during time interval $t_R$ establishing a flow of feed from the feed conduit into the first opening and a flow of a reaction product from the second opening into the reaction product conduit, and
      (ii) during a time interval $t_H$ establishing a flow of fuel from the fuel conduit into the second opening, establishing a flow of oxidant from the oxidant conduit into the second opening, and establishing a flow of combustion product from the first opening into the combustion product conduit.

2. The reverse flow reactor of claim 1, wherein the reactor vessel has the form of an elongated tube of circular, elliptical, or polygonal cross section, and wherein the reverse flow reactor further comprises at least one mixer distributor located in a flow path between the second aperture of the first channeled member and the first aperture of the second channeled member.

3. The reverse flow reactor of claim 1, wherein M is selected from the group consisting of Sc, Ti, Zr, Hf, V, Nb, Ta, Cr, Mo, and combinations thereof; A is selected from the group consisting of Al, Si, P, Ga, Ge, As, Cd, In, Sn, Tl, Pb, and combinations thereof; N is selected from the group consisting of Ti, Zr, Hf, V, Nb, Ta, and combinations thereof; P is selected from the group consisting of Ti, Zr, Hf, V, Nb, Ta, Cr, Mo, W, Mn, Tc, Re, Fe, Ru, Os, Co, Rh, Ir, Ni, Pd, Pt, and combinations thereof; and m is ≤k.

4. The reverse flow reactor of claim 1, wherein the first ceramic comprises one or more of $Ti_3SiC_2$, $Ti_2AlC$, $Nb_2AlC$, $Zr_2AlC$, $Ti_2AlC$, $V_2AlC$, $Cr_2AlC$, $Hf_2InC$, $Ti_2SC$, $V_2SC$, $Ti_3SiC_2$, $Ti_3GeC_2$, $Ti_3SnC_2$, $Ti_3AlC_2$, $Ti_2AlC$, $Ti_2AlN$, $Ti_3AlC$, $Ti_3AlN_2$, $(Nb,Zr)_2AlC$, $(Ti,V)_2AlC$, $(Ti,Nb)_2AlC$, $(Ti,Cr)_2AlC$, $(Ti,Hf)_2InC$, and $(Ti,V)_2SC$, $Ti_3(Si,Ge)C_2$, and $Ti_3(Sn,Al)C_2$, $Ti_2Al(C,N)$ and $Ti_3Al(C,N)_2$; the second ceramic comprises $ZrB_2$ and/or $HfB_2$; and the third ceramic comprises $Nb_3Al$, $Nb_2Al$, $NbAl$, $NbAl_3$, and $MoSi_2$.

* * * * *